US007206699B2

(12) United States Patent
Larder et al.

(10) Patent No.: US 7,206,699 B2
(45) Date of Patent: Apr. 17, 2007

(54) METHODS FOR MEASURING THERAPY RESISTANCE

(75) Inventors: Brendan Larder, Churchlane (GB); Stuart Bloor, Biggleswade (GB); Kurt Hertogs, Antwerp (BE); Pascale Alfons Rosa Dehertogh, Puurs (BE); Rudy Jean Marc Mortier, Laarne (BE)

(73) Assignee: Virco N.V. (BE)

( * ) Notice: Subject to any disclaimer, the term of this patent is extended or adjusted under 35 U.S.C. 154(b) by 1034 days.

(21) Appl. No.: 09/836,477

(22) Filed: Apr. 18, 2001

(65) Prior Publication Data

US 2002/0091664 A1 Jul. 11, 2002

Related U.S. Application Data

(60) Provisional application No. 60/197,606, filed on Apr. 18, 2000, provisional application No. 60/213,219, filed on Jun. 22, 2000.

(51) Int. Cl.
G06F 19/00 (2006.01)
(52) U.S. Cl. .............................. 702/19; 702/20; 702/22
(58) Field of Classification Search .................. 702/19, 702/20, 22
See application file for complete search history.

(56) References Cited

U.S. PATENT DOCUMENTS

| 5,202,259 A | 4/1993 | Goff et al. ............. 435/252.33 |
| 6,087,093 A | 7/2000 | Lieven et al. ................... 435/5 |
| 6,221,578 B1 | 4/2001 | de Bethune et al. ............ 435/5 |
| 6,869,759 B1 | 3/2005 | Parkin et al. ................... 435/5 |

FOREIGN PATENT DOCUMENTS

| EP | 0 203 200 B1 | 1/1990 |
| WO | WO 94/16737 | 8/1994 |
| WO | WO 97/27480 | 7/1997 |
| WO | WO 99/40227 | 8/1999 |
| WO | WO 99/61658 | 12/1999 |
| WO | WO 99/67427 | 12/1999 |
| WO | WO 00/73511 A1 | 12/2000 |
| WO | WO 00/78996 A1 | 12/2000 |
| WO | WO 01/16860 | 3/2001 |
| WO | WO 01/57245 A2 | 8/2001 |

OTHER PUBLICATIONS

Harrigan et al. (AIDS (1999) vol. 13, No. 14, pp. 1863-187.*
Ioannidis et al. (American Journal of Epidemiology (1998) vol. 147, No. 5, pp. 464-471.*
Boden et al. (JAMA (1999) Sep., vol. 282, No. 12, pp. 1135-1141).*
Virologic HIV Assays:Review of Report Forms).*
Hertogs et al (Antimicro. Agents and Chemo. (Mar. 2000) vol. 44, pp. 568-573).*
Harrigan et al., "Baseline HIV drug resistance profile predicts response to ritonavir-saquinavir protease inhibitor therapy in a community setting", AIDS, 13, pp. 1863-1871, (1999).

Hertogs et al., "Comprehensive HIV drug resistance monitoring using rapid, high-throughput phenotypic and genotypic assays with correlative data analysis", AIDS, 13(14), Poster Abstracts OP3.4, p. 11.
Vandamme et al., "Managing Resistance to Anti-HIV Drugs—An important Consideration for Effective Disease Management", DRUGS 1999, 57(3), pp. 337-361, (1999).
Walter et al., "Rapid, phenotypic HIV-1 drugs sensitivity assay for protease and reverse transcriptase inhibitors", Journal of Clinical Virology, 13, pp. 71-80, (1999).
Wegner et al., "Prevalence of genotypic and phenotypic resistance to anti-retroviral drugs in a cohort of therapy-naïve HIV-1 infected US military personnel", AIDS, 14, pp. 1009-1015, (2000).
Beroud, et al., "UMD (Universal Mutation Database): A Generic Software to Build and Analyze Locus-Specific Databases," Human Mutation, 2000, 15(1), 86-94.
Cohen, C. et al. 3 Abstracts, "Phenotypic Resistance Testing Significantly Improves Response to Therapy: A Randomized Trial," "Exploration of HIV-Infection as a Risk Factor for Symptomatic Plasma Cell Endometritis," "Forty-Eight Week Analysis of Patients Receiving T-20 as a Component of Multi-Drug Salvage Therapy," XIII International AIDS Conference, 2000.
D'Aquila, R.T., "HIV-1 Chemotherapy and Drug Resistance," Clinical Diagnostic Virology, 1995, 3, 299-316.
De Gruttola, V. et al., "The Relation between Baseline HIV Drug Resistance and Response to Antiretroviral Therapy; Re-Analysis of Retrospective and Prospective Studies Using a Standardized Data Analysis Plan," Antiviral Therapy, 2000, 5, 41-48.
De Leon, et al., "Clinical Features and Genotype-Phenotype Correlations in 41 Italian Families with Adenmatosis Coli," Italian Journal of Gastoenterology and Hepatology, 1990, 31(1), 850-860.
Eastman, P.S., "Comparison of Selective Polymerase Chain Reaction Primers and Differential Probe Hybridization of Polymerase Chain Reaction Products for Determination of Relative Amounts of Codon 215 Mutant and Wild-Type HIV-1 Populations," Journal of Acquired Immune Deficiency Syndrome and Human Retroviology, 1995, 9, 264-273.
Edman, P., "Sequence Determination," Mol. Biol. Biochem. Biophys, 1970, 8, 211-255.
Estellar, M. et al., "Inactivation of the DNA-Repair Gene MGMT and the Clinical Response of Gliomas to Alkylating Agents," New England Journal of Medicine, 2000, 343, 19, 1350-1354.

(Continued)

Primary Examiner—Lori A. Clow
(74) Attorney, Agent, or Firm—Yunling Ren

(57) ABSTRACT

The present invention concerns methods for measuring drug resistance by correlating genotypic information with phenotypic profiles. In one embodiment, a method for interpreting genotypic information is described wherein a genetic code is generated from a patient sample, a list of mutations known or suspect to play a role in the development of resistance to one or more drugs is obtained from the generated genetic code, a genotype database is interrogated for previous samples with similar mutations relating to said one or more drugs, a phenotype for said sample is located in a phenotype database, the mean change in inhibition is determined based on all the examples located in said phenotype database, a distribution of sensitivities of one or more drugs suitable for treating a specific indication is determined.

23 Claims, 12 Drawing Sheets

OTHER PUBLICATIONS

Fodor, S.P. et al., "Multiplexed Biochemical Assays with Biological Chips," *Nature*, 1993, 364, 555-556.

Graber, J. et al., "Differential Sequencing with Mass Spectrometry," *Genetic Analysis: Biomolecular Engineering*, 1999, 14, 215-219.

Hertogs, K. et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," *Antimicrobial Agents Chemotherapy*, 1998, 42(2), 269-276.

Hirsh, et al., "Antiretroviral Drug Resistance Testing in Adult HIV-1 Infection," *The Journal of American Medical Association*, May 2000, 283(18), 2417-2426.

Japour, A.J. et al., "Standardized Peripheral Blood Mononuclear Cell Culture Assay for Determination of Drug Susceptibilities of Clinical Human Immunodeficiency Virus Type 1 Isolates", "The RV-43 Study Group & The ACTG Virology Committee Resistance Working Group," *Antimicrobial Agents Chemotherapy*, 1993, 37, 1095-1101.

Jeanpierre, et al., "Software and Database for the Analysis of Mutation in the Human WT1 Gene," *Nucleic Acids Research*, 1998, 26(1), 271-274.

Kellam, P. et al., "Recombinant Virus Assay: A Rapid, Phenotypic Assay for Assessment of Drug Susceptibility of Human Immunodeficiency Virus Type 1 Isolates," *Antimicrobial Agents and Chemotherapy*, 1994, 38, 23-30.

King, P.J. et al., "Resistance to the Anti-Human Immunodeficiency Virus Type 1 Compound L-Chicoric Acid Results from a Single Mutation at Amino Acid 140 of Integrase," *Journal of Virology*, 1998, 72(10), 8420-8424.

Larder, B.A. et al., "Zidovudine Resistance Predicted by Direct Detection of Mutations in DNA from HIV-Infected Lymphocytes," *AIDS*, 1991, 5, 137-144.

Larder, et al., "A Complete Survey, In Over 1,500 Clinical HIV-1 Isolates, of Phenotypic and Genotypic Protease Inhibitor Resistance Profiles (Including Gag Cleavage Site Sequences) and Their Relation to Therapy History," *AIDS*, 1998, 12(4), S11, OP3.5.

Larder, B.A. et al., "Use of Neural Networks to Define the Genetic Basis of HIV-1 resistance to d4T," *Fifth International Conference on Drug Therapy in HIV Infection*, Glasgow, 2000, 14(4), PL 9.5.

Laurent-Puig Pierre, et al., "APC Gene: Database of Germline and Somatic Mutations in Human Tumors and Cell Lines," *Nucleic Acids Research*, 1998, 26(1), 269-270.

Pauwels, R. et al., "Comprehensive HIV Drug Resistance Monitoring Using Rapid, High-Throughput Phenotypic and Genotypic Assays With Correlative Data Analysis," $2^{nd}$ *International Workshop on HIV Drug Resistance and Treatment Strategies*, Lake Maggiore, Italy, Jun. 24-27, 1998, Abstract 51, 35-36.

Pauwels, R. et al., "Correlation between Genotypic and Phenotypic Resistance Data in AVANTI," *Abstracts of the Interscience Conference on Antimicrobial Agents and Chemotherapy*, 1997, 37, 263-264 I-112.

Peipkorn, M., "Genetic Basis of Susceptibility to Melanoma," *Journal of the American Academy of Dermatoloty*, 1994, 31(6), 1022-1039 (Abstract only).

Petropoulos, C.J. et al., "A Novel Phenotypic Drug Susceptibility Assay for Human Immunodeficiency Virus Type 1," *Antimicrobial Agents Chemotherapy*, 2000, 44(4), 920-928.

Petropoulos, C.J. et al., "Human Immunodeficiency Virus 1, Complete Genome," *Database Genebank NCBI*, 2000, Accession nr. NC_001802, 11 pages.

Reinke, et al., "Natural Selection Results in Conservation of HIV-1 Integrase Activity Despite Sequence Variability", *AIDS*, 2001, 15(7), 823-830.

Robertson, D.K. et al., "DNA Methylation in Health and Disease," *Nature Reviews*, 2000, 1, 11-19.

Sanger, F. et al., "DNA Sequencing with Chain Terminating Inhibitors," *Proc. Natl. Acad. Sci.*, 1977, 74, 5463-5467.

Schinazi, R.F. et al., "Mutations in Retroviral Genes Associated with Drug Resistance," *International Antiviral News*, 1997, 5(8), 129-142.

Shafer, R., "Human Immunodeficiency Virus Reverse Transcriptase and Protease Sequence Database," *Nucleic Acids Research*, 1999, 27(1), 348-352.

Skinner, et al., "Analysis of a Large Collection of Natural HIV-1 Integrase Sequences, Including those from Long-Term Nonprogressors," *Journal of Acquired Immune Deficiency Syndromes and Human Retrovirology*, 1998, 19(2), 99-110.

Stuyver, L. et al., "Line Probe Assay for rapid Detection of Drug-Selected Mutations in the Human Immunodeficiency Virus Type 1 Reverse Transcriptase Gene," *Antimicrobial Agents and Chemotherapy*, 1997, 41, 284-291.

Vandamme, A-M. et al., "Laboratory Guidelines for the Practical Use of HIV Drug Resistance Tests in Patient Follow-Up," *Antiviral Theraphy*, 2001, 6(1), 21-39.

Woerner, A.M. et al., "Characterization of a DNA Binding Domain in the C-Terminus of HIV-1 Integrase by Deletion Mutagenesis," *Nucleic Acids Research*, 1993, 21(15), 3507-3511.

Yates, J., "Mass Spectrometry from Genomics to Proteomics," *Trends in Genetics*, 2000, 16, 5-8.

\* cited by examiner

METHODS FOR MEASURING THERAPY RESISTANCE

RELATED APPLICATION DATA

This application claims priority benefit of U.S. Provisional Application No. 60/197,606, filed on Apr. 18, 2000, and U.S. Provisional Application No. 60/213,219, filed Jun. 22, 2000, the contents of which are expressly incorporated by reference herein.

FIELD OF THE INVENTION

The present invention concerns methods and systems for predicting the resistance of a disease to a therapy. More specifically, the invention provides methods for predicting therapy resistance or phenotype by correlating genotypic information with phenotypic profiles. The invention further relates to methods and systems for designing, optimizing and assessing a therapy regimen based upon the genotype of the disease affecting the patient.

BACKGROUND OF THE INVENTION

Techniques to determine the resistance of a pathogen or malignant cell to a therapy are becoming increasingly important. For example, despite the great advantages of existing treatments against viral infections such as HIV infection, cancer and bacterial infections, many patients experience treatment failure or reduced efficacy over time. In many instances this is due to the pathogen, malignant cell, bacteria, virus or other disease state mutating and/or developing a resistance to the treatment.

For example, all the drugs currently used in the HIV field were discovered and developed over a period of 15 years, starting with AZT. By the beginning of the year 2000, 15 different anti-HIV-1 agents had been approved by the FDA. Initially, and due to a lack of alternative drugs, these agents were administered alone, as monotherapy. Though a temporary antiviral effect was observed, all the compounds lost their effectiveness over time. In 1989, Larder et al. published a paper in *Science*, 246, 1155–8, incorporated by reference herein, that identified a number of mutations that caused HIV-1 resistance to AZT. Since then, research has demonstrated that one of the main reasons behind treatment failure for all the antiviral drugs is the development of resistance of the virus to the drug.

Drug resistance and drug resistant mutations develop because retroviruses such as HIV have no proofreading mechanism when synthesizing new nucleic acid strands. This allows for the continuous generation of a number of genetic variants in a replicating viral population. More importantly, the genetic changes may alter the configuration of the reverse transcriptase (RT) and protease (PR) molecules in such a way that they are no longer susceptible to inhibition by compounds developed to target them. If antiretroviral therapy is ongoing and if viral replication is not completely suppressed, the selection of genetic variants is inevitable and the viral population becomes resistant to the drug.

In the face of monotherapy failure and encouraged by a number of clinical trials, in the early-mid 1990's treatment strategy turned to combination therapy, i.e., administration of mixtures of antiviral drugs. At the time there were still only one class of drugs available—the nucleoside analogue reverse transcriptase inhibitors (NRTIs). As a result, the standard of care became two nucleosides, typically AZT+ddI (didanosine), or AZT+ddC (ditiocarb sodium). Dual combination therapy provided increased control of viral replication, made it more difficult for the virus to develop resistant strains or mutations and, as a result, provided extended clinical benefit to patients.

In 1995, another milestone was reached with the approval of the first of the protease inhibitors (PIs). These inhibitors showed greater potency than the nucleosides, but again were prone to resistance when used alone. Their combination with two nucleoside analogues, however, seemed to provide the control over the virus that everyone had been looking for. Triple combination therapy using two nucleosides (most commonly AZT+3TC) plus a protease inhibitor (typically indinavir) still remains the most common standard of care in developed countries.

These highly active combinations have had an enormous effect on the quality of life and on the survival of patients. This has resulted in fewer hospitalizations and reintegration of the patients in society. In a considerable number of patients, the viral load has been reduced to below the detection limit for prolonged periods.

In recent years, however, it has become clear that even patients being treated with triple therapy including a protease inhibitor often eventually experience treatment failure. Data suggests that up to one half of patients on combination therapy do not achieve or do not maintain suppression of virus replication. In some cases, it may be that even state-of-the-art triple therapy is insufficient to halt viral replication. As a result, drug resistant strains of the virus develop.

Another factor contributing to the difficulty to maintain suppression of virus replication has been the sheer burden of taking up to 20 pills each day, at set times, with or without food, day after day. It is simply unrealistic to expect people to adhere to such stringent and demanding regimens indefinitely. But if patients do not adhere, the price can be high. A dip in the blood levels of any of the medications gives the virus an opportunity to replicate and develop drug resistant strains. As such, during the course of infection, drug resistant viral strains can emerge very rapidly particularly for retroviral infections such as HIV-1. In addition, not all HIV-1 infections originate with a wild type, drug sensitive strain from which drug resistance will emerge. With the increase in prevalence of drug resistant strains comes the increase in infections that actually begin with drug resistant strains. Infections with pre-existing drug resistance immediately reduce the drug options for drug treatment and emphasize the importance of drug resistance information to optimize initial therapy for these patients.

Moreover, as the number of available antiretroviral agents has increased, so has the number of possible drug combinations and combination therapies. However, it is not easy for the health care provider to establish the optimal combination for an individual. Previously, the only treatment guidelines that have been in widespread use have been based on viral load and, where available, the patient's treatment history. The health care provider's objective is to keep the viral load as low as possible. An increase in viral load is a warning that control of viral replication is being lost and that a change in therapy is required. Viral load, however, provides no information or guidance regarding which drugs should be used.

Knowledge of the resistance patterns of different inhibitors and the patient's treatment history can help. Resistance emergence is highly predictive of treatment failure. In fact, while there are a variety of factors that can contribute to the failure of drug therapy, HIV-1 drug resistance is almost always involved. However, the interactions between different viral mutations related to different inhibitors is so complex that selecting the optimal treatment combination with only a treatment history to go on is far from ideal. Drugs can be ruled out unnecessarily and ineffective drugs can be introduced. Even if the virus is resistant to just one of three drugs in a treatment regimen, this can allow low-level viral replication to take place and viral strains resistant to the other two drugs to develop.

It is clear that although there are many drugs available for use in combination therapy, the choices can quickly be exhausted and the patient can rapidly experience clinical deterioration if the wrong treatment decisions are made. The key to tailored, individualized therapy lies in the effective profiling of the individual patient's virus population in terms of sensitivity or resistance to the available drugs. This will mean the advent of truly individualized therapy.

The aim of resistance monitoring is to provide the necessary information to enable the health care provider to prescribe the most optimal drug combination for the individual patient. At present, there are two distinct approaches to measuring resistance:

The first approach involves phenotyping, which directly measures the actual sensitivity of a patient's pathogen or malignant cell to particular therapies. For example, HIV-1 phenotype testing directly measures HIV-1 drug resistance, detected as the ability of HIV-1, taken from a patient, to grow in the presence of a drug, in the laboratory. The phenotype is measured or expressed in, for example, $IC_{50}$ for a particular drug, which is defined as the concentration of drug required to kill half of the virions in a sample. This is compared to the $IC_{50}$ for the drug using wild type virus. The phenotype may be described, but is not limited to, fold increase in $IC_{50}$ for each of the drugs.

There are three main types of methodology for phenotyping. One such type is the plaque reduction assay. A drawback of this method is that it does not detect NSI strains. Another method of phenotyping includes PBMC p24 growth inhibition assays (Japour, A. J., Mayers, T. L., Johnson, V. A., Kuritzkes, D. R., Beckett, L. A., Arduino, J.-M., Lane, J., Black, R. J., Reichelderfer, P. S., D'Aquila, R. T., Crumpacker, C. S., The RV-43 Study Group & The ACTG Virology Committee Resistance Working Group. *Antimicrob. Agents Chemother.* 37, 1095–1101 (1993), incorporated by reference herein). A problem with this technique is that virus culture from PBMCs is very slow and labor-intensive. In addition, it lacks the precision of other techniques and because it relies on primary human cells for virus growth, assay automation and high throughput is virtually impossible. Yet another method is the recombinant virus assay (Kellam, P. & Larder, B. A. *Antimicrob. Agents Chemother.* 38, 23–30 (1994), incorporated by reference herein.). The recombinant method has advantages over the previously mentioned assays in that it reduces the amount of selection that takes place during growth of the virus in the laboratory, it is faster, more reproducible, amendable to automation and high throughput, and all available drugs can be tested in one assay.

The second approach to measuring resistance involves genotyping tests that detect specific genetic changes (e.g. but not limited to, mutations) in the viral genome, which lead to amino acid changes in at least one of the target proteins, known or suspected to be associated with resistance.

There are a number of techniques for conducting genotyping, such as hybridization-based point mutation assays and DNA sequencing. Common point mutation assays include Primer-specific PCR (Larder B A, Kellam P & Kemp, S D 1991. *AIDS* 5: 137–144, incorporated by reference herein.), differential hybridization (Eastman, P. S., Urdea, M., Besemer, D., Stempien, M. & Kolberg, J. 1995. *J. Acquir. Immune Defic. Syndr. Human Retrovirol.* 9, 264–273, incorporated by reference herein.), Line Probe Assay (LiPA®, Innogenetics) (Stuyver, L., Wyseur, A., Rombout, A., Louwagie, J., Scarcez, T., Verhofstede, C., Rimiand, D., Schinazi, R. F. & Rossau, R. 1997. *Antimicrob. Agents Chemotherap.* 41, 284–291, incorporated by reference herein.), and gene chip sequencing (Affymetrix) (D'Aquila, R. T. 1995. *Clin. Diagnost. Virol.* 3, 299–316, incorporated by reference herein.). Point mutation assays can only provide a small select part of the resistance picture. DNA sequencing, however, provides information on all the nucleotides in the region of the genome sequenced. This means that changes in the genome can be detected. It also means that, in contrast to point mutation assays, as new resistance mutations are found to be involved in the development of HIV-1 drug resistance, these can still be detected without adaptation of the technology (unlike point mutation assays).

However, at present, it remains difficult to interpret the results of a genotypic test to provide meaningful conclusions about therapy resistance. The advantage of phenotyping over genotyping is that phenotyping is a direct measure of any change in sensitivity resulting from all the mutations that have occurred, and any interactions between them. As such, it is the gold standard of resistance testing. Disadvantages of phenotyping are that it is complex, lengthy to perform, (usually 4 weeks) and, therefore, more expensive than genotyping. Thus, phenotyping is not a practical way of designing patient therapy.

The importance of the speed by which a health care provider can be informed of the patient's resistance profile can be demonstrated by the following hypothetical but realistic example, which highlights the need to reduce complexity and improve performance time of assessing resistance. Suppose first-line triple combination therapy reduces the viral load to undetectable limits for a period of time. The viral load then begins to increase as a result of the development of resistance. Without resistance information, the health care provider can make a judgement based on the patient's treatment history, and change one or more of the drugs. As a result viral load is, again, reduced but the new treatment regimen is sub-optimal so viral replication continues under selection pressure from the drugs and resistance rapidly develops once more. Consequently, control of viral replication is lost and several of the 15 drugs available have been 'used up'.

Although genotyping tests can be performed more rapidly, a problem with genotyping is that there are now over 100 individual mutations with evidence of an effect on susceptibility to HIV-1 drugs and new ones are constantly being discovered, in parallel with the development of new drugs and treatment strategies. The relationship between these point mutations, deletions and insertions and the actual susceptibility of the virus to drug therapy is extremely complex and interactive. An example of this complexity is the M184V mutation that confers resistance to 3TC but reverses AZT resistance. The 333D/E mutation, however, reverses this effect and can lead to dual AZT/3TC resistance.

Consequently, the interpretation of genotypic data is both highly complex and critically important. There have been a number of different approaches to this challenge of interpretation. For example, armed with the knowledge of the main resistance mutations associated with each drug and the patient's recent treatment history, a health care provider makes a decision as to the optimum treatment. To assist health care providers to make these judgments, various expert opinion panels have been convened and have published guidelines, e.g. the Resistance Collaborative Group. In addition, rules-based algorithms constitute another approach. This is essentially a formalized version of the above with tables giving the mutations which are associated with resistance to each of the drugs. These can be simple printed tables or the information can be used to develop a rules-based computer algorithm. However, given the large number of mutations that are involved in resistance to antiretroviral drugs and given the complex interactions between the mutations, the shortcoming of genotyping is the reliable interpretation and clinical application of the results. As more drugs become available and as more mutations are involved in the development of resistance, the 'manual' or rules-based interpretation of raw genotype data is rapidly becoming impossible due to an increase in complexity.

Therefore, the main challenge involved with genotyping is improving the interpretation of the results. The technology will identify some (i.e., point mutation assays) or all of the mutations (i.e., DNA sequencing) that have occurred but it then requires sophisticated interpretation to predict what the net effect of these mutations might be on the susceptibility of the virus population to the various therapies. A health care provider might then have to combine this information with all the other information relating to the patient and decide what all this means in terms of selecting drugs for the treatment of their individual patient.

SUMMARY OF THE INVENTION

An example of a solution to the problems set forth above involves new methods for measuring therapy resistance by correlating genotypic information with phenotypic profiles. In one embodiment, the invention provides a method of determining a phenotype of a biological sample comprising: a) obtaining a genetic sequence of the biological sample; b) identifying a mutation pattern of the genetic sequence of the biological sample, wherein said mutation pattern comprises at least one mutation that correlates to resistance to at least one therapy; c) searching a relational genotype/phenotype database for at least one database mutation pattern similar to said mutation pattern of the genetic sequence of the biological sample, wherein said search identifies at least one database mutation pattern; d) obtaining at least one database phenotype of the at least one database mutation pattern from the relational genotype/phenotype database; and e) determining the phenotype of the biological sample from the at least one database phenotype. Steps b) through e) may be repeated in order to determine a phenotype for each therapy in a group of therapies.

In another embodiment, the invention provides a method of determining a phenotype of a biological sample comprising: a) obtaining a genetic sequence of the biological sample; b) searching a relational genotype/phenotype database for at least one database genetic sequence similar to said genetic sequence of the biological sample, wherein said search identifies at least one database genetic sequence; c) obtaining a database phenotype of the at least one database genetic sequence; and d) determining the phenotype of the biological sample from the database phenotype.

The invention also provides a method of assessing effectiveness of a therapy on a patient, comprising: a) obtaining a genetic sequence of a biological sample from the patient; b) identifying a mutation pattern of the genetic sequence of the biological sample, wherein the mutation pattern comprises at least one mutation that correlates to resistance to at least one therapy; c) searching a relational genotype/phenotype database for at least one database mutation pattern similar to said mutation pattern of the genetic sequence of the biological sample, wherein said search identifies at least one database mutation pattern; d) obtaining at least one database phenotype of the at least one database mutation pattern; e) determining the phenotype of the biological sample to the therapy from the at least one database phenotype; and f) determining whether the phenotype of the biological sample is in a therapeutically effect range.

In another embodiment, the invention provides a method of optimizing therapy for a patient, comprising: a) obtaining a genetic sequence of a biological sample from the patient; b) identifying a mutation pattern of the genetic sequence of the biological sample, wherein the mutation pattern comprises at least one mutation that correlates to resistance to at least one therapy; c) searching a relational genotype/phenotype database for at least one database mutation pattern similar to said mutation pattern of the genetic sequence of the biological sample, wherein said search identifies at least one database mutation pattern; d) obtaining at least one database phenotype of the at least one database mutation pattern; e) determining the phenotype of the biological sample to the therapy from the at least one database phenotype; f) repeating steps b) through e) for a group of therapies to obtain a series of phenotypes for the biological sample; and g) selecting an optimal therapy for the patient from the series of phenotypes.

A method of designing a therapy for a patient is also provided, which comprises: a) obtaining a genetic sequence of a biological sample of the patient; b) identifying a mutation pattern of the genetic sequence of the biological sample, wherein the mutation pattern comprises at least one mutation that correlates to resistance to at least one therapy; c) searching a relational genotype/phenotype database for at least one database mutation pattern similar to said mutation pattern of the genetic sequence of the biological sample, wherein the mutation pattern comprises at least one mutation that correlates to resistance to at least one therapy; d) obtaining at least one database phenotype of the at least one database mutation pattern; e) determining the phenotype of the biological sample from the at least one database phenotype; f) repeating steps b) through e) for a group of therapies to obtain a series of phenotypes for the biological sample; and g) designing a therapy for the patient from the series of phenotypes.

The invention further relates to systems, computer program products, business methods, server side and client side systems and methods for generating, providing, and transmitting the results of the above methods.

Both the foregoing general description and the following detailed description are exemplary and are intended to provide further explanation of the invention as claimed.

BRIEF DESCRIPTION OF THE DRAWINGS

The accompanying drawings provide a further understanding of the invention and are incorporated in and constitute a part of this specification. The drawings, together with the description, illustrate various embodiments of the invention. In the drawings:

FIG. 1(*b*) is an exemplary flow chart of one embodiment for performing steps 110 to 130 of FIG. 1(*a*).

DEFINITIONS

Figure 1A:
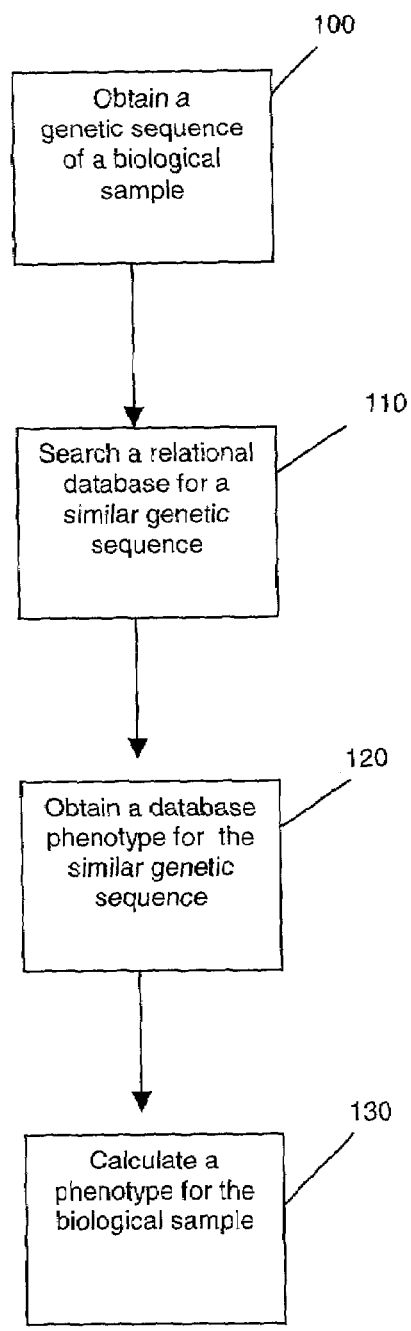
FIG. 1(*a*) is an exemplary flow chart for determining a phenotype, in accordance with the methods of the invention.

A "biological sample" is any material obtained from a patient comprising a disease producing agent. A biological sample may be obtained from, for example, saliva, semen, breast milk, blood, plasma, feces, urine, tissue samples, mucous samples, cells in cell culture, cells which may be further cultured, etc. In one embodiment, for a patient infected with HIV, any biological sample containing virus may be used. In another embodiment, for a cancer patient, a sample may include all of the above, and tumors, biopsy tissue, etc. from which the sequence of tumor suppressing genes could be determined.

A "genetic sequence" is any sequence containing at least one nucleotide. A nucleotide, for example, may be represented by the letters A, C, T, G, or U. A combination of nucleotides, may be represented, for example, by other letters such as R, Y, M, etc. Genetic sequence as used herein may refer to a sequence of a biological sample, such as, for example, the complete sequence of a disease producing agent or at least one segment of the sequence of a disease producing agent. Amino acids can be represented either by their three letter or one letter codon, see Alberts et al: Molecular Biology of the Cell, Garland Publishers, N.Y. 1994.

A "communication channel" is any channel which allows communication between different people, computers, or locations, i.e., telephone lines, wireless networks, computer networks, public networks (such as the Internet), private networks (such as an intranet), satellite-based networks, manual entry of data into a common database, etc. This communication channel may be digital or analog, real time or delayed, and one way or two way, or any combination or combinations thereof between the different entities.

The term "health care provider" is understood to include any professional person authorized or trained to treat or take patient data and/or samples. Such persons include but are not limited to physicians, doctors, clinicians, health care workers, nurses, technicians, laboratories, etc.

A "phenotype" includes any observable property of an organism or disease producing agent that is produced by the genotype in conjunction with the environment. In one embodiment, phenotype refers to resistance of a disease producing agent to at least one therapy.

A "virtual phenotype" is a phenotype that is obtained from genotypic data through the correlation of genotype of a sample. In one embodiment, for example, a "virtual phenotype" is a phenotype of a sample that is obtained through the determination of the genotype of said sample, wherein said genotype is used for correlation in a database to search for matching genotypes for which a corresponding phenotype is known. From this collection of phenotypes, the virtual phenotype of the sample is calculated.

A "disease producing agent" is any agent causing illness or disease that is amenable to therapy resistance testing. Examples of disease producing agents include but are not limited to viruses such as retroviruses, cancer causing genes or gene mutations such as those found in p53 and other oncogenes or tumor suppressor genes, proteins, bacteria, viruses, prions, algae, fungi, protozoa and other agents which result in an infectious disease.

"HIV" is the human immunodeficiency virus, which is a retrovirus.

"Retrovirus" is any RNA virus that utilizes reverse transcriptase during its life cycle.

A "patient" is any organism, particularly a human or other mammal, suffering from a disease or in need or desire of treatment for a disease. A patient includes any mammal, including farm animals or pets, and includes humans of any age or state of development.

"Phenotypic resistance" comprises resistance to a tested therapy of a biological sample, such as a disease producing agent, including by not limited to a cell, a malignant cell, a virus, or a virally infected cell. A skilled artisan will recognize that phenotypic resistance may be expressed by any number methods including, but not limited to, resistance, fold resistance, and $IC_x$, such as $IC_{50}$ and $IC_{90}$.

A "therapy" includes but is not limited to a drug, pharmaceutical, antiviral, anti-bacterial, antibiotic, anticancer, anti-fungal, or other compound or composition, or a treatment, such as gene therapy or radiation therapy, useful for the treatment or amelioration of a disease in a patient. Therapy, as used herein, also includes combination therapies.

"Resistance" as used herein, pertains to the capacity of resistance, sensitivity, susceptibility, or effectiveness of a therapy against a disease.

A "relational genotype/phenotype database" refers to a database that brings together the knowledge of both a genotypic and phenotypic database. A relational genotype/phenotype database may, for example, comprise one database, two databases, or more than two databases. The genotypic database, or the genotype field of a database, for example, may contain genetic sequence information regarding at least one tested disease producing agent. The genetic sequence information may vary from the entire sequence of a disease producing agent to a segment of the sequence of a disease producing agent, to a mutation pattern. In one embodiment, the genetic sequence information may comprise the genetic sequence of tested HIV viruses or the mutation pattern of tested HIV viruses. The phenotypic database, or the phenotype field of a database, for example, may contain phenotypic resistance values for the at least one tested disease producing agent to at least one therapy. For example, the phenotypic resistance values of tested HIV viruses, with a fold resistance determination compared to the reference HIV virus (wild type).

In one embodiment, in a relational genotype/phenotype database, the data entries are combined to yield a "2D" representation for each sample: ($x_i$, $y_i$) where $x_i$ represents the phenotypic result, $y_i$ the genotypic. In another embodiment, the data entries are combined to yield a "3D" representation for each sample: ($x_i$, $y_i$, $z_i$) where $x_i$ represents the phenotypic result, $y_i$ the genotypic result, and $z_i$ other information regarding the sample, such as a sample number. In one embodiment, for example, the relational genotype/phenotype database may constitute different genotype and phenotype databases.

The term "mutation," as used herein, encompasses both genetic and epigentic mutations to a disease causing agent. A genetic change includes, but is not limited to, (i) base substitutions: single nucleotide polymorphisms, transitions, transversions, substitutions and (ii) frame shift mutations: insertions, repeats and deletions. Epigenetic changes include, but are not limited to, alterations of nucleic acids, e.g., methylation of nucleic acids.

"At least one mutation that correlates to resistance to at least one therapy" includes, but is not limited to, mutations and combination of mutations in a genetic sequence that influence sensitivity of a disease causing agent to a therapy. The at least one mutation may influence sensitivity to a specific therapy, e.g., a drug, or a group of therapies. The at least one mutation may, for example, increase and/or decrease resistance of a disease causing agent to a therapy. The at least one mutation, may also, for example, enhance and/or decrease the influence of other mutations present in a genetic sequence that affect sensitivity of a disease causing agent to a therapy.

For example, the influence of mutations on the etiology of cancer can be exemplified by the mutations influencing the effect of the tumor suppressor gene such as p53, TGF-beta, NF-1, WT-1, and Rb. Also, mutations present in oncogenes such as Ras, c-myc, c-raf, neu, and IL-2, and repair genes, e.g., methylguanosyl and methyltransferase can cause changes in the phenotype and/or drug effect. In another embodiment, a mutation that is a methylation of nucleic acids may occur at the 5-position of cytosine within the CpG-dinucleotide. In general the CpG dinucleotide is greatly under-represented throughout the mammalian genome, but it can be found at close to its expected frequency in small genomic areas of about one kilobase, called CpG islands. Although the CpG islands account for only about 1% of the complete genome and for 15% of the total genomic CpG sites, these regions contain approximately 50% of the unmethylated CpG dinucleotides. Methylation, may for example, impact disease states, such as Fragile X and Rett syndrome, and also on drug profiling. See for example, Robertson et al., *Nature Reviews,* 2000 vol 1, p. 11–19, and Esteller M. et al. *New England Journal of Medicine,* 2000, Vol 343:19, p. 1350–1354, the disclosures of which are hereby incorporated by reference.

In one embodiment, the at least one mutation that correlates to resistance to at least one therapy includes mutations or combinations of mutations that are known or suspected in the art to influence the sensitivity to a therapy. Lists of mutations known or suspected in the art to influence the sensitivity of a disease causing agent to a therapy may be found, for example, in the scientific literature, patents, and patent applications. For example, mutations known or suspected in the art to influence the sensitivity of HIV to a therapy may be found in, Schinazi, R. F., Larder, B. A. & Mellors, J. W. 1997. *Int. Antiretroviral News* 5, 129–142 (1997); Schinazi et al., *Intl. Antiretroviral News* 7, 46–69 (1999); Shafer et al., *Nucleic Acid Research,* 27(1), 348–352 (1999); WO 00/78996; WO 99/67427; WO 99/61658; U.S. Pat. No. 6,087,093; WO 00/73511; and U.S. patent application Ser. Nos. 09/580,491, 09/589,167 and 60/241,844, now U.S. Pat. No. 7,058,616 the disclosures of which are hereby incorporated by reference. Examples of mutations known or suspected in the art to influence the sensitivity of HIV to a therapy may also be found on the internet at hiv-web.lanl.gov; hivdb.stanford.edu/hiv/; or viral-resistance.com. RT domain of HIV conferring resistance to a reverse transcriptase inhibitor include, but are not limited to, 69 C, 69 V, 69 T, 75A, 101I, 103T, 103N, 184T, 188H, 190E, 219 N, 219 Q, 221Y, 221I, and 233V. Additional examples of mutations present in the PR domain of HIV conferring resistance to a reverse transcriptase inhibitor include, but are not limited to, 24M, 48A, and 53L. A mutation may effect resistance alone or in combination with other mutations. The specific therapy, for example an antiretroviral drug, for which a mutation may effect resistance may be determined by one of skill in the art, for example, using the a phenotypic resistance monitoring assay such as, the ANTIVIROGRAM®.

In one embodiment, a more accurate phenotype may be obtained by constructing a mutation pattern using mutations that have been validated. One of skill in the art will recognize that there are numerous methods of validating whether a mutation correlates to resistance to at least one therapy, including but not limited to phenotype experiments, such as the ANTIVIROGRAM®(K. Hertogs et al., *Antimicrobial Agents and Chemotherapy,* 42(2): 269–279 (1998), the entire disclosure of which is hereby incorporated by reference) (Virco, Belgium) and clinical studies.

In another embodiment, the number and the combinations of mutations used to construct a mutation pattern would be updated on a regular basis. This may be done in order to incorporate newly identified mutations or combinations which may improve the performance of the system. In one embodiment, a phenotype may be calculated from at least one mutation used to construct a mutation pattern, however, from a statistical perspective a more accurate phenotype may result from a greater number of mutations.

A "mutation pattern" comprises at least one mutation influencing sensitivity of at least one disease causing agent to at least one therapy. In one embodiment, a mutation pattern is a list of mutations or a list of combinations of mutations that influence sensitivity of at least one disease causing agent to at least one therapy. A mutation pattern may be constructed, for example, by searching a genetic sequence for the occurrence of each mutation of a series of mutations. The existence of a mutation or the existence of one of a group of mutations may then be noted. The mutation pattern is constructed, for example, once a genetic sequence is searched for the occurrence of each mutation in the series. In one embodiment, a mutation pattern is constructed using a group of mutations that correlate to resistance to a therapy, thereby constructing a mutation pattern that is specific to a therapy. In a further embodiment, a mutation pattern is constructed by searching for mutations in a genetic sequence wherein the mutations are linked by at least one logical operator chosen from AND, OR, NOT, and NOR.

"Similar," as used herein in reference to similar mutation patterns and similar genetic sequences, means, in one embodiment, a mutation pattern and/or a genetic sequence that has the same effect towards resistance to therapies. Similar mutation patterns may include, for example, mutations patterns with at least one matching mutation. Similar genetic sequences, may include, for example, genetic sequences with at least one matching mutation and/or a similar sequence may selected by sequence alignment or multiple sequence alignment as described herein.

A "therapy profile" is the combination of mutation patterns corresponding to resistance to a single therapy.

The "control sequence" or "wild type" is the reference sequence from which the existence of mutations is based. For example, the control sequence for HIV may be HXB2. This viral genome comprises 9719 bp and has an accession number in Genbank at NCBI M38432 or K03455 (gi number: 327742). Assays for detection of mutations in HIV-1 may be based on polymerase chain reaction (PCR) amplification of viral genomic sequences. These amplified sequences may then be analyzed using either hybridization or sequencing techniques. Hybridization-based assays include, for example, primer-specific PCR, which makes use of synthetic oligonucleotides designed to allow selective priming of DNA synthesis. See Larder, B. A., et al., *AIDS* 5, 137–144 (1991); Richman, D. D., et al., *J. Infect. Dis.* 164, 1075–1081 (1991); Gingeras, T. R., et al., *J. Infect. Dis.* 164, 1066–1074 (1991). In this embodiment, only when primer sequences match the target sequence (wild-type or mutant) at the 3' end, is amplification of target sequences possible and DNA fragments are produced. Knowledge of the primer sequences allows one to infer the sequence of the viral isolate under investigation, but only for the region covered by the primer sequences. Other hybridization-based assays include differential hybridization (Eastman, P. S., et al., *J. Acq. Imm. Def. Syndr. Human Retrovirol.* 9, 264–273 (1995); Holodniy, M., et al., *J. Virol.* 69, 3510–3516 (1995); Eastman, P. S., et al., *J. Clin. Micro.* 33, 2777–2780(1995).); Line Probe Assay (LiPA□ HIV-11 RT, Innogenetics) (Stuyver, L., et al., *Antimicrob. Agents Chemotherap.* 41, 284–291 (1997).); Oligonucleotide ligation assay (Edelstein, R. et al. *J. Clin Microbiol.* 36(2), 569–572 (1998)) and GeneChip technology (Affymetrix) (D'Aquila, R. T. *Clin. Diagnot. Virol.* 3, 299–316 (1995); Fodor, S. P. A. et al., *Nature* 364, 555–556 (1993); Fodor, S. P. A. *Nature* 227, 393–395 (1997).

DNA sequencing assays, on the other hand, provides information on all nucleotides of the sequenced region. Target sequences are amplified by PCR. Sequence analysis is primarily based on the incorporation of dideoxy chain-terminating nucleotides (lacking 3' hydroxyl groups) in elongating DNA sequences and gel-electrophoretic analysis of the resulting molecules. Most sequencing technologies are semi-automated and make use of fluorescently labeled primers or ddNTPs to "read" off the sequence from a polyacrylamide gel. Novel techniques and approaches to determine mutations are being developed and are evenly well suited to determine mutations present in a sample under investigation. Other assays to determine mutations that have become available include, for example, Invader® assay (Third Wave Technologies, Inc.), WAVE® DNA assay (Transgenomic, Inc.), mass spectrometry (Jackson P., et al. *Molecular Medicine Today* 6, 271–276, (2000)) and surface plasmon resonance (Nakatani, K. et al. *Nature Biotechnology* 19(1), 18–19, (2001). An overview of currently used mutation techniques, comprising gel based and non-gel based analyses are surveyed in Shi, M. *Clin. Chem.* 2001, (47:2) 164–172.

"Codon" as used herein refers to the position of the amino acid present at that specific location of the gene investigated, e.g., a mutation at codon 90 of the protease gene refers to the an altered amino acid at position 90 in the protein chain as compared to the wild type gene.

The genetic sequence of a biological sample, if the biological sample is a particular target protein, may be obtained by either sequencing the nucleic acid coding for the target protein or by sequencing the protein itself. Protein sequencing may be obtained for example but not limited to classical Edman degradation chemistry. Edman P. *Mol. Biol. Biochem. Biophys.* 8, 211–255 (1970). This chemistry can also be fully automated. Novel techniques including mass spectroscopy also enable the analysis of the sequence of a protein under investigation. Yates J., *Trends in Genetics*, 16, 5–8 (2000). Alternatively, the sequence of a target protein can be obtained using classical nucleic sequencing protocols e.g. extension chain termination protocols (Sanger technique, Sanger F., Nichler., Coulson A. *Proc. Nat. Acad. Sci.* 74, 5463–5467 (1977)) or chain cleavage protocols. A particular sequencing methodology was developed by Visible Genetics using only 3 out of 4 bases for sequencing. Other novel approaches that have been developed for unravelling the sequence of a target nucleic acid include, but are not limited to, mass spectrometry, MALDI-TOF (matrix assisted laser desorption ionization time of flight spectroscopy) (Graber J, Smith C., Cantor C., *Genet. Anal.*, 14, 215–219 (1999).) chip analysis (hybridization based techniques) (Fodor S P et al., *Nature* 364, 555–6 (1993)). Nucleic acid sequencing includes both DNA and RNA sequencing.

DETAILED DESCRIPTION OF THE INVENTION

In one embodiment, the present invention provides a thorough and reliable interpretation of genotypic information by interrogating the genotype part of a relational genotype/phenotype database for identical or similar patterns of mutations to that of the patient sample under study. Once the matches are found, the corresponding phenotypes may be accessed and the phenotypic information, such as the changes in $IC_{50}$ to the various therapies, may be pooled and averaged to produce a phenotypic profile or a virtual phenotype. This profile, for example, may be based on data from hundred or thousands of real phenotypes with the same patterns of mutations. In one application of the invention, for example, the HIV-1 genome of a patient sample is sequenced, or a particular region of the genome such as the RT-PR region, and the sequence is used in the methods of the invention to interpret the genotype information and determine the virtual phenotype.

In one embodiment, the virtual phenotype may be used to design a therapy. In other embodiments of the invention, a virtual phenotype may be used to assess the effectiveness of a therapy or optimize a therapy. In a further embodiment, proprietary software may be used to interpret the genotype information according to the methods of the invention. The methods of the invention may also be used, for example, in a business method of a computer program. The methods and systems may also be used to generate reports, including reports on computer readable media.

The methods of the invention, in one embodiment, bring together the knowledge of both a genotypic and a phenotypic database, i.e., a relational genotype/phenotype database, and determines a virtual phenotypic fold resistance value without actually having to do phenotypic testing. For example, in one embodiment, this analysis may be done by comparing the sequence of the biological sample sequence under test, e.g. from a patient HIV virus sample, against the stored sequences and by selecting "similar sequences". Phenotypic data is then gathered for those "similar sequences" and the virtual phenotype may be calculated from the selected phenotypic values. In one embodiment, the similar sequences are ranked, for example, by number of matching mutations or % identity of the genetic sequences. The sequences with most matching mutations and/or the highest % identity may then be used to calculate the virtual phenotype.

In one embodiment, for example, a virtual phenotype may be calculated by taking the mean fold resistance of the phenotypic data gathered from the stored sequences. A phenotype may also, for example be calculated by taking the median fold resistance of the phenotypic data gathered from the stored sequences This value is called "Virtual Fold Resistance", which leads to the "Virtual Phenotype."

In another embodiment, for example, the log of the standard deviation of all the fold resistance values is calculated from the phenotypic data gathered from the stored sequences:

$$\sqrt{\frac{n\sum x^2 - (\sum x)^2}{n(n-1)}}$$

where n is the amount of phenotypic determinations and x contains the individual fold resistance values. The mean, for example, of all the fold resistance values may then be calculated and the outliers are determined using a value of $3\dot{O}$, which are the fold resistance values that are greater than (mean+(3×STD)) or smaller than (mean−(3×STD)). The corrected mean fold resistance may be calculated on all the data minus the outliers and the corrected value may be reported and used to determine resistance together with the cut-off values corresponding to this therapy. A corrected median fold resistance may also be calculated, for example, using the same procedure.

A similar sequence may selected, in one embodiment, by sequence alignment or multiple sequence alignment. Similar in this context does not usually mean exactly alike. In one embodiment, a similar genetic sequence is at least about 60% identical to the sequence of interest, including at least about 70% identical, at least about 80% identical, and at least about 90% identical. More information regarding sequence alignment and multiple sequence alignment may be found, for example in "Bioinformatics: A practical guide to the analysis of genes and proteins" Eds. Baxevanis and Ouellette, 1998, John Wiley and Sons, New York (Chapter 7 "Sequence alignment and database searching" G. Schuler; Chapter 8 Practical "Aspects of multiple sequence alignment" A. Baxevanis; and Chapter 9 "Phylogenetic analysis" M. Hershkovitz and D. Leipe). A practical example of multiple sequence alignment is the construction of a phylogenetic tree. A phylogenetic tree visualizes the relationship between different sequences and can be used to predict future events and retrospectively to devise a common origin. This type of analysis may be used to predict a similar therapy sensitivity for a sample and also to unravel the origin of a different patient sample (i.e. the origin of the viral strain).

In another embodiment, "Discrete Clustering" is used to determine when sequences are "similar". Rather, "similar", in this context, means "having similar mutations", which are mutations that have the same effect towards resistance against therapies. In one embodiment, this is accomplished by identifying a mutation pattern for a genetic sequence of a biological sample and search a relational genotype/phenotype database for similar mutation patterns. A similar mutation pattern is a mutation pattern with at least one matching mutation. However, a better match may be obtained by matching more than one mutation. For example, a similar mutation pattern may have at least two of the same mutations as the mutation pattern of interest including, at least about 50% identical mutations, at least about 60% identical mutations, at least about 70% identical mutations, at least about 80% identical mutations, and at least about 90% identical mutations. In one embodiment, the mutations of one mutation pattern may be identical to the mutations of the mutation pattern of interest.

For example, a pattern database that is therapy related may be built. In one embodiment, the patterns of mutations may be referred to as "hot spots". The hot spots describe mutations or clusters of mutations (generally combined by "OR" (|) or "AND" (&) logical operators) that are related to a certain therapy. A therapy may have 1, 2, 3, 4 or more hot spots attached to it. Other logical operators may be "NOT", "NOR" etc. and the possibility to identify INSERTS and DELETIONS in the DNA sequence.

A simplified example of the hot spots table follows:

| Therapy | # | Hot spot |
|---------|---|----------|
| A | 1 | (mutationD | mutationE) &(mutationF | mutationG) |
|   | 2 | mutationH | mutationI |
|   | 3 | mutationJ & mutationK |
|   | 4 | (mutationZ | mutationX) & mutationV |
| B | 1 | mutationL |
|   | 2 | mutationM & mutationN |
|   | 3 | (mutationO & mutationP) | mutationQ |
| C | 1 | mutationR |
|   | 2 | mutationS | mutationT |

Subsequently, every target sequence, e.g., HIV virus sequence, that is tested is "profiled" by testing the sequence against all the available hot spots, for all the therapies involved. This analysis produces a mutation pattern or profile per therapy for the sequence of interest.

In the embodiment, for every hot spot that matches, the sequence receives a "1"; for every non-matching hot spot, it gets a "0". For a given sequence, th result could be:

| Therapy | Mutation Pattern | |
|---------|------------------|---|
| A | 1010 | hot spots 1 and 3 apply for drug A, hot spots 2 and 4 do not. |
| B | 001 | hot spot 3 applies for drug B, hot spots 1 and 2 do not. |
| C | 10 | hot spot 1 applies for drug C, hot spots 2 does not. |

In other words, a mutation pattern can be given for each therapy. In the example of therapy A above, hot spots 1 and 3 relate to resistance to therapy A and are assigned a value of 1. In contrast, hot spots 2 and 4 do not and are assigned a value of 0, thus the mutation pattern "1010". This procedure can be seen as a form of clustering. However, since the elements of the cluster (0 and 1) are based on pre-defined sets (hot spots) this method is usually referred to as "discrete clustering." After determining the mutation pattern for a sequence under test, the relational genotype/phenotype database (or the sequence (or genotypic) database part of a relational genotype/phenotype database) may be queried for sequences similar to the sequence under scrutiny. This query may, for example, be accomplished using cluster searches.

In another embodiment, a number of hot-spots is defined for a specific therapy. In a further embodiment, the hot-spots are continuously updated. To compare the sequences, a list of mutation patterns (one mutation pattern per therapy that is tested) is determined for every genetic sequence. The mutation pattern is determined by keeping count of matching and non-matching hot spots per therapy. In this example, there are 10 hot spot descriptions related to the therapy in question.

| | |
|---|---|
| Therapy A | Mutation A \| Mutation B \| Mutation C \| Mutation D |
| | Mutation E \| Mutation F |
| | Mutation G & Mutation H |
| | (Mutation I \| Mutation J) & (Mutation K \| Mutation L) |
| | Mutation M \| Mutation N \| Mutation E \| Mutation F |
| | (Mutation M \| Mutation N \| Mutation E \| Mutation F) & Mutation G |
| | Mutation O & Mutation P |
| | Mutation Q \| Mutation R \| Mutation F |
| | Mutation E & Mutation Q & Mutation G |
| | Mutation R |

In the above example, if a genetic sequence would match hot spot 2, 5, 6, 7 and 9, the sequence would have a mutation pattern for this therapy equal to '0100111010'. In one embodiment, every new mutation pattern is stored inside a database. In a further embodiment, every hot-spot keeps count of the sequences that match the hot-spots mutation. Using this information, the system may retrieve all the sequences that have exactly the same mutation pattern by doing an intersection of the sets that match and by subsequently subtracting the sets that don't match. Instead of using sets of sequences, the systems may use the corresponding sets of phenotypic data. This may increase the performance of the system. In one embodiment, the system is a dynamic system, i.e., the accuracy of the system may be increased by regularly updating the hotspots.

Regardless of the method used to select "similar sequences", once a selection of "similar sequences" is found, the database phenotype is obtained, for example, by querying the relational genotype/phenotype database for phenotypic data belonging to those sequences. In one embodiment, this process is done for each therapy, again using cluster searches. The query returns a selection of phenotypic results for every therapy of interest. A statistical analysis may be performed on the data to remove outliers and the virtual fold resistance may be calculated. For example, per therapy, the mean of the log (fold resistance values) may be used to calculate the virtual fold resistance and the interpretation of these numbers will generate a Virtual Phenotype. In a further embodiment, the virtual phenotype may then further be used to classify the virus as Sensitive (S), Intermediate (I) or Resistant (R).

The present invention has broad applicability to any disease state where it is desired to correlate genotypic information with phenotypic profiles. One skilled in the art could readily take the following discussion of the invention with the HIV virus and through the exercise of routine skill apply this invention to other diseases (such as other viral infections, malignant cells, cancer, bacteria infections, other pathogens, and the like) to correlate genotypic information to predict phenotypic response, assess therapy resistance, and eventually develop a treatment regime of therapies for a particular patient. The present invention, in one embodiment, therefore, gives the health care provider the best possible interpretation of the genotype data and the best possible support for treatment decision making.

In one embodiment, the systems and methods described are very dynamic and the databases for use in practicing the invention may be frequently updated to incorporate new mutations which improve the accuracy of the determination. The systems and methods of the invention may, for example, provide a health care provider a means to optimize the therapy which will be most successful. Thus, for the treatment (or monitoring of therapy) of diseases like cancer, bacterial and viral infections, which are disease states that are subject to complex and continuously varying therapy regimens, the patient under treatment needs to undergo frequent therapy monitoring in order to follow the therapy effect or in order to optimize or select the optimal patient management.

Figure 1B:
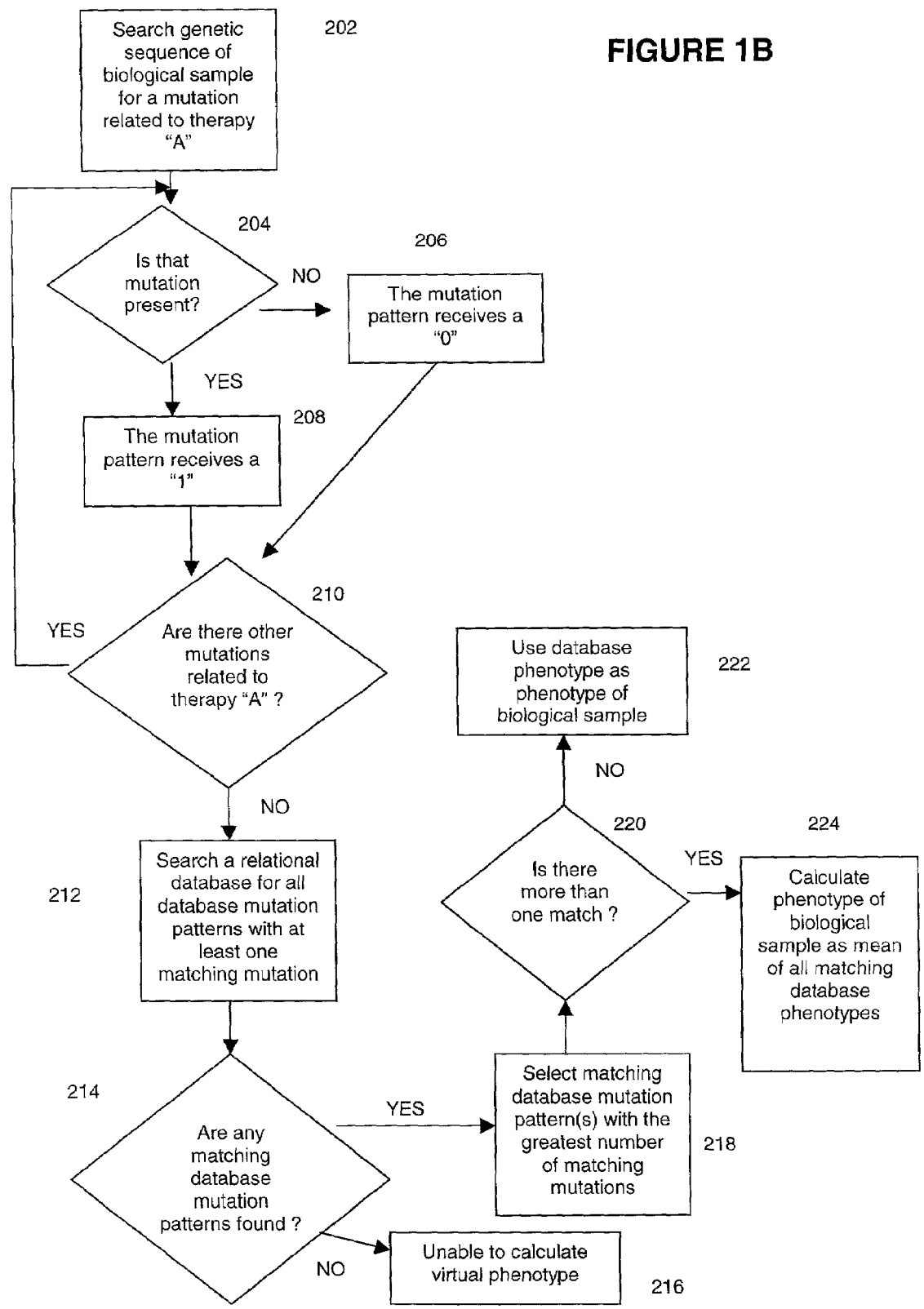

FIG. 1 provides an exemplary flowchart for determining a virtual phenotype. FIG. 1(b) is an exemplary flow chart describing one example of the use of a mutation pattern for performing steps 110 to 130 of FIG. 1(a). In one embodiment, the various steps and operations of FIG. 1 may be performed by the phenotype determination system 40 in the system environment of FIG. 2 to assess resistance of a patient to a therapy, or design or optimize a therapy for a patient, for example, with HIV.

As illustrated in FIG. 1, in one embodiment the process starts with obtaining at least one genetic sequence of a patient(step 100). A genetic sequence may be obtained by a health care provider, laboratory, or any other entity. In one embodiment, the at least one genetic sequence, including genetic sequences taken at various times or a history of sequences of a patient may be stored in a database, such as local database 46 of phenotype determination system 40 (see FIG. 2).

As part of computing a virtual phenotype, a relational genotype/phenotype database is then searched for at least one genetic sequence similar to the genetic sequence of the patient (step 110). All similar sequences may be identified. This may be accomplished by searching the relational database for a mutation pattern similar to the mutation pattern of the biological sample, or, for example, by comparing the genetic sequence of the patient to sequences of the relational genotype/phenotype database using sequence alignment. The relational genotype/phenotype database may be accessed from a local database 46 and/or 46 and/or public database(s) 52.

As illustrated in FIG. 1, a database phenotype is obtained for each similar genetic sequence identified from the relational genotype/phenotype database (step 120). A phenotype for the genetic sequence of the patient is then calculated from all of the database phenotypes identified (step 130).

Steps 110 to 130 may, for example, in one embodiment, be determined using the method described in FIG. 1b. Here a mutation pattern of the genetic sequence of a biological sample may be determined for at least one therapy. As part of this process, the phenotype determination system 40 may include data of mutations that correlate to resistance to at least one therapy. The mutation data may be accessed from local database 46 and/or public database(s) 52. The process exemplified is similar to the example described above where a pattern database that is therapy related may be built using patterns of mutations referred to as "hot spots". For example, a mutation pattern for each therapy is constructed in steps 202 to 210 for a biological sample. The mutation pattern consists of a series of 1's and 0's, which indicates the presence or absence of a mutation, respectively. In steps 212 to 218, a genotype/phenotype relational database is searched for matching mutation patterns and the database phenotypes for the closest matches are obtained. The phenotype of the biological sample is then calculated from the database phenotypes in steps 220 to 224.

The information may then be transmitted back to the health care provider or used in the determination of other information, such as to assess resistance of a patient to a therapy, or to design or optimize a therapy for a patient. The resulting information may then be transmitted back to the health care provider.

Figure 2:
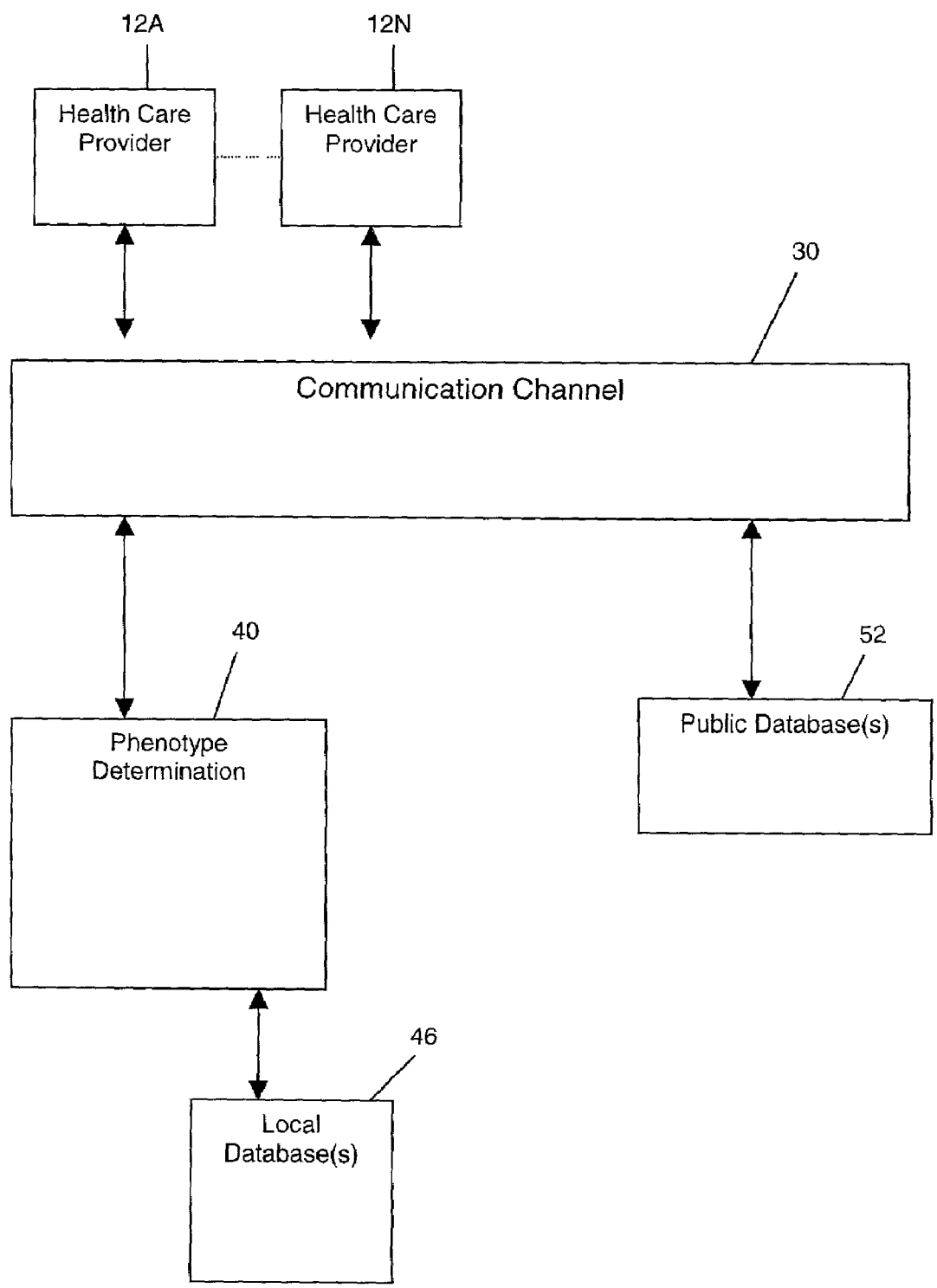
FIG. 2 is an exemplary representation of a system environment in which the features and methods of the invention may be implemented.

FIG. 2 is an exemplary system environment in which the features and methods of the invention may be implemented (for example, the methods as shown in FIG. 1). As illustrated in FIG. 2, a communication channel 30 is provided for facilitating the transfer of data between various system components and entities. These components and entities may include, for example, one or more health care providers 12A–12N who interact with or treat patients (not shown), a phenotype determination system 40, and one or more public databases 52.

Communication channel 30 may be implemented through any single or combination of channels that allow communication between different people, computers, or locations. The communication channel may be any system that allows communication between the different entities illustrated in FIG. 2.

Each of the health care providers 12A–12N, for example, collects biological samples for each patient or patients, and determines a genetic sequence or has a genetic sequence determined, wherein such data is submitted for analysis by phenotype determination system 40.

In one embodiment, the phenotype determination system 40 may be implemented through any suitable combination of hardware, software and/or firmware. For example, phenotype determination system 40 may be implemented through the use of a personal computer, a working station, a server or any other computing platform. Software or programmed instructions may also be provided for controlling the operations of the computing platform, consistent with the principles of the invention. As illustrated in FIG. 2, phenotype determination system 40 may also include a local database 46 for storing patient data including genetic sequence data. Local database 46 may also store mutation data and/or relational genotype/phenotype data mutation data and/or relational genotype/phenotype data may be accessed from one or more public databases 52 by phenotype determination system 40.

Consistent with the methods of the present invention, phenotype determination system 40 is configured to provide information regarding at least one of: phenotype, assessment of resistance of a patient to a therapy, and design or optimization of a therapy for patients treated by health care providers 12A–12N. The information may be sent by system 40 to health care providers 12A–12N in numerous formats (e.g., written report (including the examples described herein), electronic file, graphical display, etc.) and may be provided to health care providers on fee basis or as a free or ancillary service.

Another embodiment of the present invention can be described by the following steps:
1. The gag-RT-PR sequence is entered into a computer as a text string;
2. The computer program scans the sequence for all mutations, and 'lists' all those that are known or suspected to play a role in the development of therapy resistance;
3. The mutations are then listed against each of the therapies for which they affect sensitivity;
4. For each therapy, the computer program interrogates a relational genotype/phenotype database for previous samples with the same or similar, mutations, mutation patterns or sequences, relating to that therapy. Primary mutations, those initial mutations that have a discernable effect on therapy resistance, are searched in the database individually first. Secondary mutations, those that have subtle effects on resistance or increase viral fitness, are searched in groups. Typically there will be several hundred records that match the pattern of mutations for each therapy;
5. Every time a match is found, for example, a previous sample with the same or similar pattern of AZT mutations, the computer program locates the phenotype for that sample in the phenotype database and stores it (expressed as a change in $IC_{50}$)
6. Finally, again for each therapy, the program calculates the mean change in $IC_{50}$ from all the examples it has found and summarizes the distribution of sensitivities as the percentage that were sensitive (resistance is unlikely), intermediate (resistance is uncertain) or resistant (resistance is likely); and
7. The program may then generate a final report that lists, for each therapy in turn:
   A) The therapy names
   B) The mutations found in the genotype that affect sensitivity to that therapy
   C) The number of genotypes in the relational genotype/phenotype database for which phenotype data is available
   D) The proportion of these that were sensitive, intermediate or resistant to that therapy
   E) The mean sensitivity score—as a change in $IC_{50}$.

The invention also provides, in one embodiment, a method of assessing effectiveness of a therapy on a patient by determining whether the phenotype of a biological sample is in a therapeutically effect range. A therapeutically effective range takes into account, among other variables, the therapy or therapies being examined, individual patient characteristics such as a patient's pharmacokinetics, and resistance of the disease causing agent. One of skill in the art may calculate a therapeutically effective range by using, for example, published therapy effectiveness ranges and pharmacokinetic models. (See e.g., European Patent Application No. 00/203200.1, filed on Sep. 15, 2000, the disclosure of which is hereby incorporated by reference.) The invention also provides methods of optimizing therapy for a patient and designing therapy for a patient. In one embodiment, the skilled artisan may optimize and/or design a therapy by comparing the phenotypes determined using the methods of the invention and choosing the therapy or therapies that would be most effective for treating a patient.

In order to demonstrate embodiments of the invention, an example is presented which describes the optimization of treatment of HIV. Another example shows how the present invention includes methods for the optimization of treatment of other diseases, such as cancer and other malignancies. One of skill in the art will recognize that the present invention can also be used in connection with the treatment of other diseases, and that various modifications can be made (such as the use of a neural network) in order to optimize therapy for individual patients.

Figure 3:
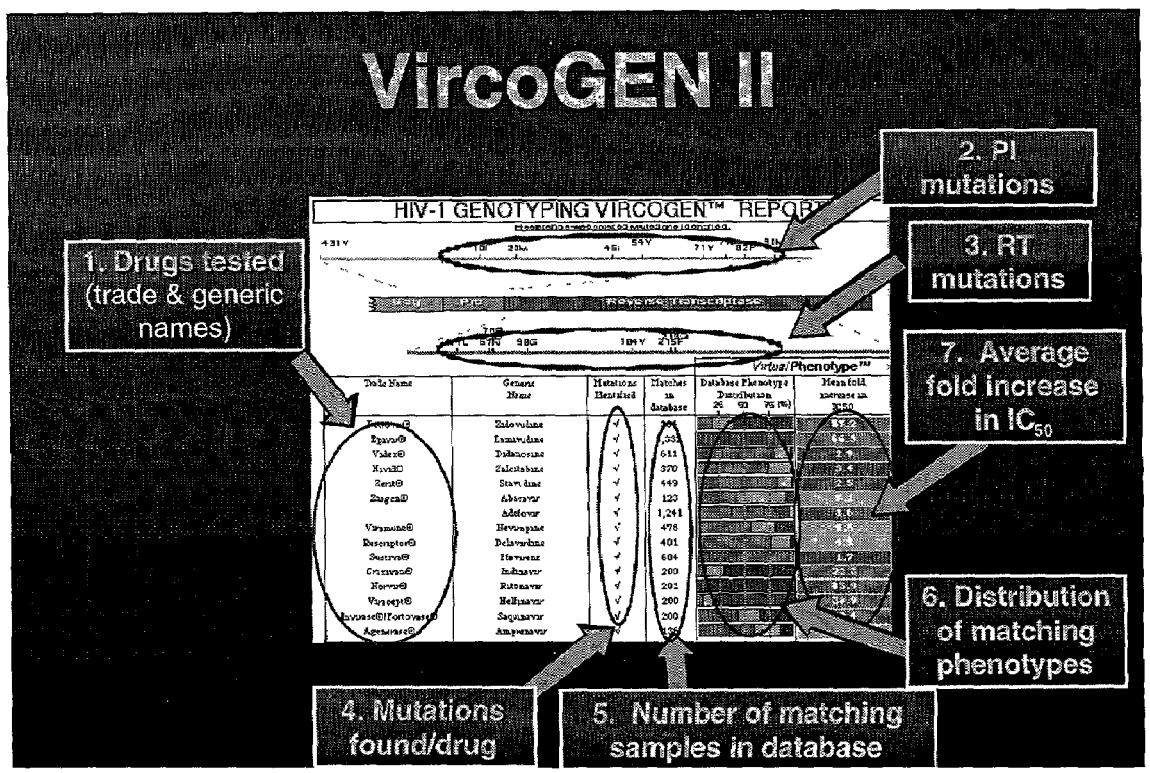
FIG. 3 is an exemplary report that provides information to aid the health care provider.

FIG. 3 is an exemplary report produced using the present invention that provides the following information to aid the health care provider in interpreting the genotypic data and developing a treatment regime:
1. The first two columns give the trade and generic names of the drugs.
2. The top of the chart has a graphic representation of the mutations in the protease region of the genome.
3. Below this is the same information for the reverse transcriptase region.
4. The third column simply indicates whether or not mutations affecting susceptibility for that particular drug were found.
5. The fourth column indicates the number of samples in the relational genotype/phenotype database that match mutation pattern in the sample virus, for each drug.
6. The fifth column has a color-coded representation of the range of phenotypic susceptibilities found in the relational genotype/phenotype database.
7. Finally the average $IC_{50}$ for all the matches in the relational genotype/phenotype database is presented for each drug.

Studies have shown the present inventive method to be more than 90% accurate in predicting the actual phenotype using a current relational genotype/phenotype database. As more data is added to a relational genotype/phenotype database, the chances of finding large numbers of exact matches for the mutational pattern of an individual will increase and the level of accuracy can be even higher.

Figure 4:
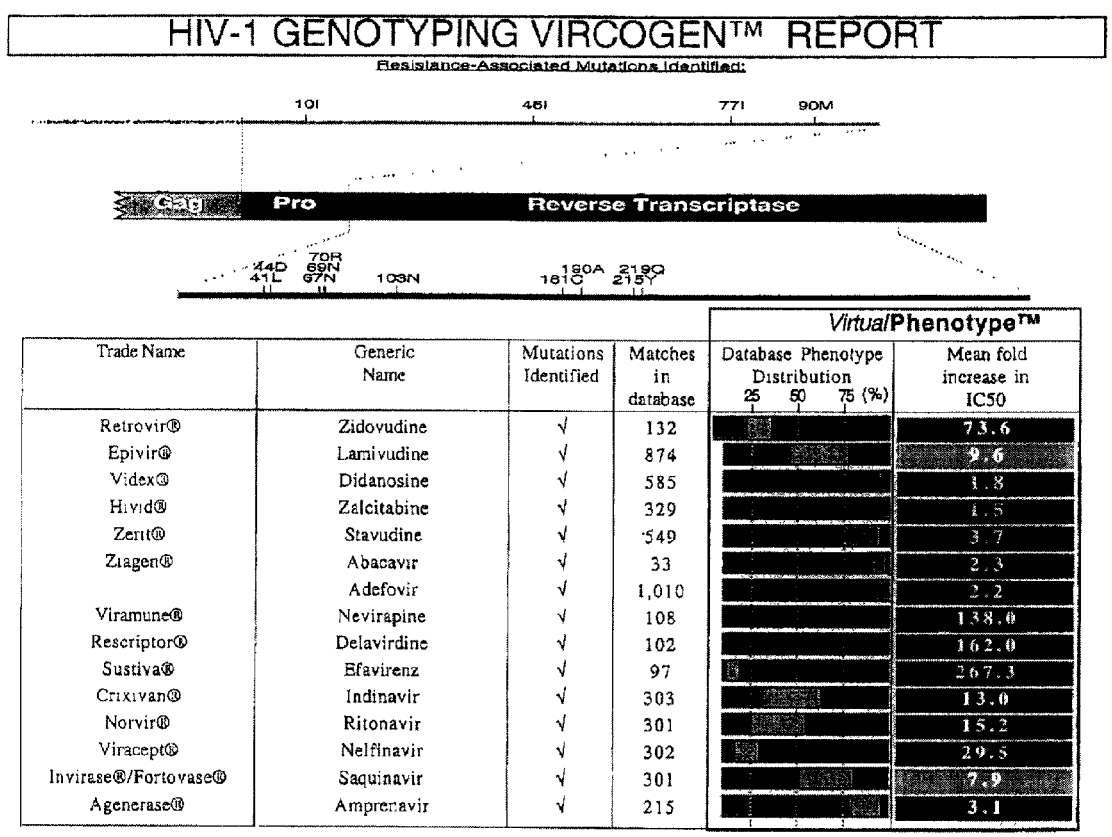
FIG. 4 is a example of a phenotypic report using the present invention.

In the case shown in FIG. 4, for example, the virus population is likely to respond to didanosine, zalcitabine, and stavudine (from the NRTIs), not AZT, 3TC and possibly not abacavir. A response is likely to any of the NNRTIs but the drug most likely to be effective is efavirenz. The patient's virus will very likely be resistant to the protease inhibitor nelfinavir and most likely to be sensitive to amprenavir.

The distribution of the sensitivities of the phenotype matches can generally enable the health care provider, regardless of the disease studied, to select among alternative therapies that the system predicts will be effective to minimize the chances of resistance. With regard to HIV, for example, two protease inhibitors may have an identical score for the predicted change in $IC_{50}$, suggesting sensitivity, but one may have a wider spread of data, including some examples where there was resistance. The health care provider can then choose the therapy with no evidence of resistance in the database.

Figure 5:
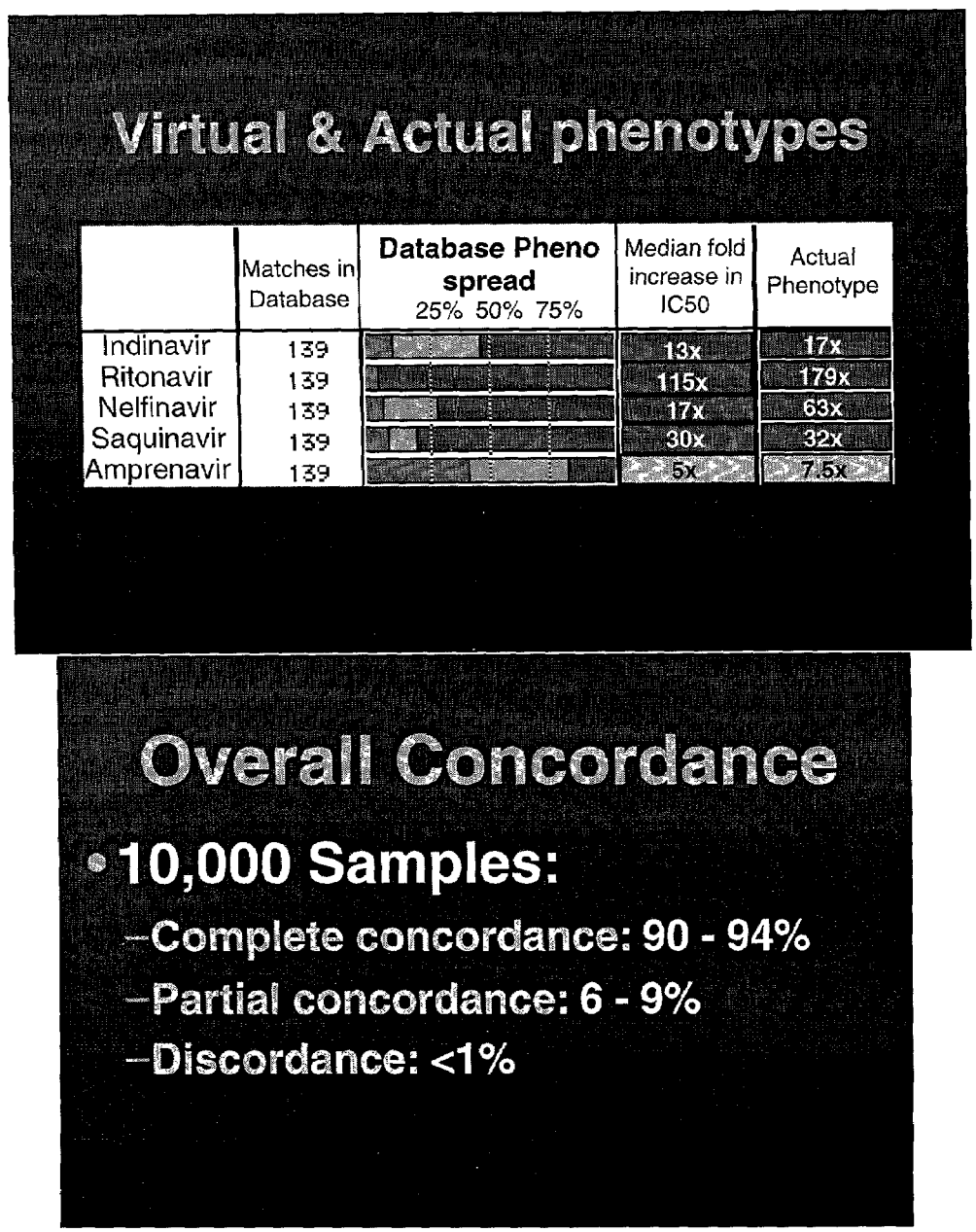
FIG. 5 is an example of the predictive value of the present invention.

This mean sensitivity score is highly predictive of the actual phenotype and is therefore a reliable predictor of which therapies the patient will or will not respond to in the clinical setting. See FIG. 5.

Figure 6:
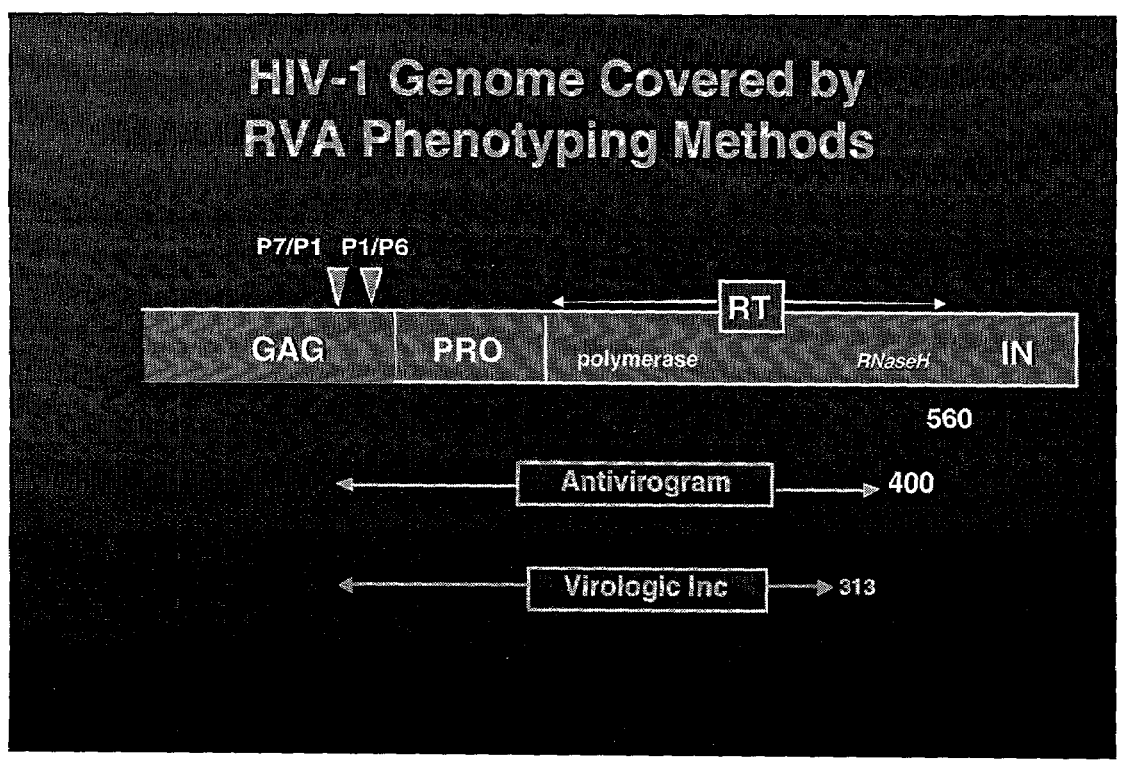
FIG. 6 is the section of the HIV genome covered by the ANTIVIROGRAM® assay.

In another embodiment, the present invention can be used with phenotypic resistance monitoring assays, such as known recombinant assays, in the clinical management of resistance developing diseases, including HIV and other viral infections, cancer, bacterial infections, and the like. A particularly useful resistance monitoring system is a recombinant assay known as the ANTIVIROGRAM®. The ANTIVIROGRAM® is a highly automated, high throughput, second generation, recombinant assay that can measure susceptibility, especially viral susceptibility, to all the available therapies, particularly antiretroviral drugs (reverse transcriptase inhibitors and protease inhibitors) at the same time. (Hertogs K, de Bethune M P, Miller V et al. *Antimicrob Agents Chemother,* 1998; 42(2):269–276, incorporated by reference). The whole process can be divided into three phases: molecular biology, transfection and susceptibility testing. The process is summarized below and in FIG. 6.

Molecular Biology
  Viral RNA fragments extracted from patient's blood sample
  Complementary DNA (cDNA) of the gag-PR-RT sequence, through to codon 400 formed via reverse transcription
  Gag-PT-RT sequence multiplied using two rounds of PCR
  Purification of the DNA fragments
  Creation of laboratory proviral clone with gag-PR-RT sequence deleted
  Insertion of the clone into bacterial plasmids for reproduction of large quantities.

Transfection
This is the process by which viral genes are transferred to a cell.
1. The gag-PR-RT sequences from the patient sample and the plasmid fragments are mixed with CD4+, MT4 cells.
2. Electroporation takes place: the cells are subject to a short (milliseconds), but strong current in a cuvette producing transient openings in the cell membrane, through which both the gag-PR-RT DNA fragment and the plasmid fragment enter.
3. In a relatively small proportion of the cells, both fragments will meet up and, probably supported by a cellular enzyme, recombine to form a complete HIV-1 genome that can now be converted into infectious virus particles.
4. The recombinant virus is then grown in this cell culture for approximately 8 days, until the cytopathogenic effect or CPE reaches a sufficient level.
5. The medium is then centrifuged to separate out the cells and the supernatant contains large quantities of recombinant virus—the virus stock harvest.
6. The virus is then titrated to achieve a known concentration.

Susceptibility Testing
In this phase, it is determined if the different HIV-1 inhibitors are still capable of inhibiting replication of the recombinant viruses mentioned above.
1. Different concentrations of the antiviral agents are placed in the 384 microwells of a microtiter test plate. Several wells are used for each concentration and the mean results used to increase reliability.
2. A set dilution of the recombinant virus stock or wild type control virus is added to each microwell.
3. A set dilution of MT4 cells containing a fluorescent reporter gene system is also added to each microwell.
4. The plate is incubated for 3 days during which time the recombinant virus will replicate in the MT4 cells unless inhibited by the antiviral drug. Replication triggers the reporter gene, which produces proteins which fluoresce.
5. The amount of viral replication at each concentration of drug is measured by computerized spectrophotometry, relative to the wild type virus controls.
6. The susceptibility of the virus to each drug is expressed as a fold change in $IC_{50}$ relative to wild type virus.
7. A report is prepared which provides these data for each drug with an increase in $IC_{50}$ of less than 4 classified as sensitive between 4 and 10 classified as intermediate and over 10 as resistant.

The whole process is highly automated and uses state of the art robotics to ensure consistency and high throughput.

Another assay exists that allows for simultaneous testing of susceptibility to reverse transcriptase inhibitors and protease inhibitors on a large scale: Virologics's 'Phenosense' assay (Petropoulos, C J, Parkin N T, Limoli K L, et al.

*Antimicrob Agents Chemother*, 2000; 44(4):920–928, incorporated by reference herein.). The assay can be described as follows:

1. Viral RNA fragments are extracted from the patient's blood sample.
2. Complementary DNA (cDNA) of the gag-Pr-RT sequence to codon 300 is formed via reverse transcription.
3. Reverse transcriptase (RT) and protease (Pr)sequences are multiplied using PCR.
4. Sample RT-Pr sequences are ligated (joined) to provirus with the RT-Pr sequences deleted and an indicator gene, luciferase inserted in the deleted HIV-1 envelope gene.
5. These recombinant viral vectors, together with a plasmid carrying the envelope proteins of murine leukemia virus, are transfected into humans cells in the presence of varying concentrations of protease inhibitors.
6. Viral particles that are formed are harvested and allowed to infect target cells for a second time in the presence of various concentrations of RT inhibitors.

Susceptibility of the viral sequences to RT inhibitors and protease inhibitors is calculated by measurement of luciferase activity.

It is desired to provide health care providers and people living with diseases, in particular HIV/AIDS, with the most accurate, reliable and useful information about the individual person's disease to help them make the most informed decision about the optimal treatment strategy and to design treatment strategies. Thus, for example, in one embodiment, the present invention (one embodiment of which is the VircoGEN II® (Virco, Belgium)) and phenotypic resistance monitoring (such as the ANTIVIROGRAM®), may be used in combination in the clinical management of diseases including diseases treated with complex drug regimens or diseases where the drug regimens needs frequent adjustment or adaptation to the changing susceptibility of the drug targets, such as HIV/AIDS. The selection of which test(s) to use and when is for the health care provider and his patient to make and depends on a number of different factors.

Recommendations for resistance testing are included in various treatment guidelines including those of the US Department of Health and Human Services and the International AIDS Society. They make no recommendations for which test to use other than the DHHS guidelines stating that the use of both tests is useful for people with complex treatment histories. The use of both phenotyping and genotyping is generally regarded as the most reliable approach to resistance testing.

Some examples of clinical situations where resistance testing could be of value are shown in table 1 with an example of a rational for the type of test to use.

TABLE 1

Example of clinical situations where resistance testing might be considered.

| Clinical situation | Assay/service | Rationale |
|---|---|---|
| Acute infection | VircoGEN II® | At this point there is usually a high viral titer and any mutant virus that has been transmitted can be readily detected. |
| Initiation of therapy | VircoGEN II® | At this point the patient is likely to have virus that is predominantly wild type or has a few mutations. It is, therefore, likely that the relational genotype/phenotype database will have large numbers of matching records and that a VirtualPhenotype ® will be highly reliable. |
| Sub-optimal response to potent combination therapy | VircoGEN II® or BOTH | If the initial regimen was selected on the basis of genotypic information, then an ANTIVIROGRAM ® should be run. If the initial selection was made without resistance information then a VircoGEN II may be sufficient. |
| Treatment failure | VircoGEN II® | Again, when a patient's treatment regimen begins to fail, in most cases the number and complexity of the mutations are likely to be similar to samples in the relational genotype/phenotype database, so the number of matches and the predictability of the VP will be high. |
| Treatment failure in patients with very complex treatment histories | BOTH | In this situation an ANTIVIROGRAM ® is essential and running both tests would be best. Conducting both tests means that the one can act as a check for the other. This combination will give how viruses with that pattern of mutations have 'behaved' in the past and how this particular virus 'behaves' in the presence of drugs under controlled laboratory conditions. |
| When new drugs are introduced | BOTH | In this situation there is likely to be a scarcity of information about the patterns of mutations involved in resistance-an ANTIVIROGRAM ® would be essential and running both tests would be best. This would provide as much information as possible about the molecular basis of resistance to the new drug as well as informing clinical decision-making. |
| Few matches for the individual's genotype | ANTIVIROGRAM ® | In a small minority of cases a genotype may reveal a novel pattern of mutations such that there are insufficient matches in the relational genotype/phenotype database to produce a statistically reliable VirtualPhenotype ®. In these cases, an ANTIVIROGRAM ® is recommended. |

EXAMPLE 1

Sample Source and Susceptibility Analysis

Plasma samples were obtained from patients and submitted to laboratories for routine assessment of drug susceptibility. These were collected mainly from the USA, Canada and Europe, although samples from South America, South East Asia and South Africa are also represented in the relational genotype/phenotype database. Due to the nature of collection of these samples, comprehensive therapy and clinical histories from the majority of the patients involved could not be obtained—although most were from different individual patients. Viral RNA was extracted from these samples and converted to cDNA by reverse transcription. Subsequently, a 1.7 kb fragment of the HIV-1 genome that encompassed part of gag, the protease and the first 400 codons of RT was amplified by PCR. These amplicons were directly sequenced by ABI automated sequencing and the drug susceptibility phenotype was determined for 14 individual antiretroviral drugs, using a recombinant virus assay. Text sequences were imported directly into the relational genotype/phenotype database, as were the $IC_{50}$ and fold resistance values for each drug.

Database Development and Derivation of Virtual Phenotype

The relational genotype/phenotype database was developed in a RAD (Rapid Application Development) environment using Apple Macintosh. Programming was in "4$^{th}$ Dimension" (4D); a 32-bit, graphical, multi-threaded relational database. The database currently runs on a PowerMac G4, 400 MHz, 256 MB RAM. For the purposes of the analysis, the software assumed that the mixture of a wild type and mutant amino acid at a particular residue was mutant. A total of 108 individual, different amino acid changes were used in the search procedure (at a total of 56 unique positions). This was broken down into 39 changes in the protease and 69 in the RT (32 for the non-nucleoside RT inhibitors and 37 for the nucleoside analogues). The following mutations, grouped by drug class, were included in the search engine. Protease inhibitors: 10F/I/R/V, 20I/M/R/T, 24I, 30N, 32I, 33F/I/M/V, 36I, 46I/L, 47L, 48V, 50V, 54L/M/V, 71T/V, 73A/C/S, 77I, 82A/F/S/T, 84A/V, 88D/S, 90M. Nucleoside analogues: 41L, 44A/D, 62A, 65R, 67N, 69D/N, 69 insertion, 70R, 74V/I, 75A/I/M/T, 77L, 100I, 115F, 116Y, 118I, 151M, 181C, 184I/T/V, 208Y, 210W, 211K/Q, 215F/Y, 219E/N/Q, 333D/E. NNRTIs: 98G/S, 100I, 101E/I/P/Q, 103N/Q/R/S/T, 106A/I/L, 108I, 179D/E, 181C/I/V, 188C/H/L, 189I, 190A/E/S, 225H, 233V, 236L, 238T. At the time of the study, the relational genotype/phenotype database comprised ~45,000 phenotyped and ~35,000 genotyped samples, of which >15,000 had both a genotype and phenotype.

DAP Analysis of Clinical Samples

Viral load data of clinical samples from 191 patients who participated in the VIRA 3001 prospective HIV-1 phenotyping study were analysed according to the data analysis plan of the international resistance collaborative group. Complete phenotypic and genotypic data were available for these patients, who received a total of 635 antiretroviral drugs. The analysis parameter was virological failure at week 16, defined as plasma HIV-1 RNA above 400 copies/ml. Logistic regression was used to model this parameter. In the univariate models, the total genotypic sensitivity score (genotype analysis) or the phenotypic sensitivity score (real phenotype and virtual phenotype analysis) were the only factors in the model. Whereas, in the multivariate models, baseline HIV-1 plasma viral load and number of new drugs in the treatment regimen were added as extra covariates. To calculate the genotypic sensitivity score, particular mutations, or groups of mutations, were used to designate resistance or susceptibility to each antiretroviral drug in the regimen (these were pre-defined by the resistance collaborative group). Phenotypic sensitivity scores for both the actual phenotypes and virtual phenotypes were based on the fold change in $IC_{50}$ relative to a wild type, susceptible virus control. The total phenotypic score was defined as the number of susceptible drugs in the regimen.

Derivation of the 'Virtual Phenotype'

Firstly, the protease and reverse transcriptase (RT) regions of the HIV-1 genome were sequenced by standard methods. These regions code for the enzymes targeted by the current antiretroviral drugs and mutations here can confer drug resistance. Mutations associated with resistance present in the sequence were identified and then software searched a relational genotype/phenotype database for archived samples with a similar mutation pattern for each drug (a mixture of wild type and mutant amino acid is treated as fully mutant). Because of the substantial size of the database, typically hundreds or thousands of matches were found. The software then retrieved the phenotypic data for each of the matching genotypes drug by drug, performed a logarithmic transformation and calculated a transformed mean fold-change in resistance.

Figure 7:
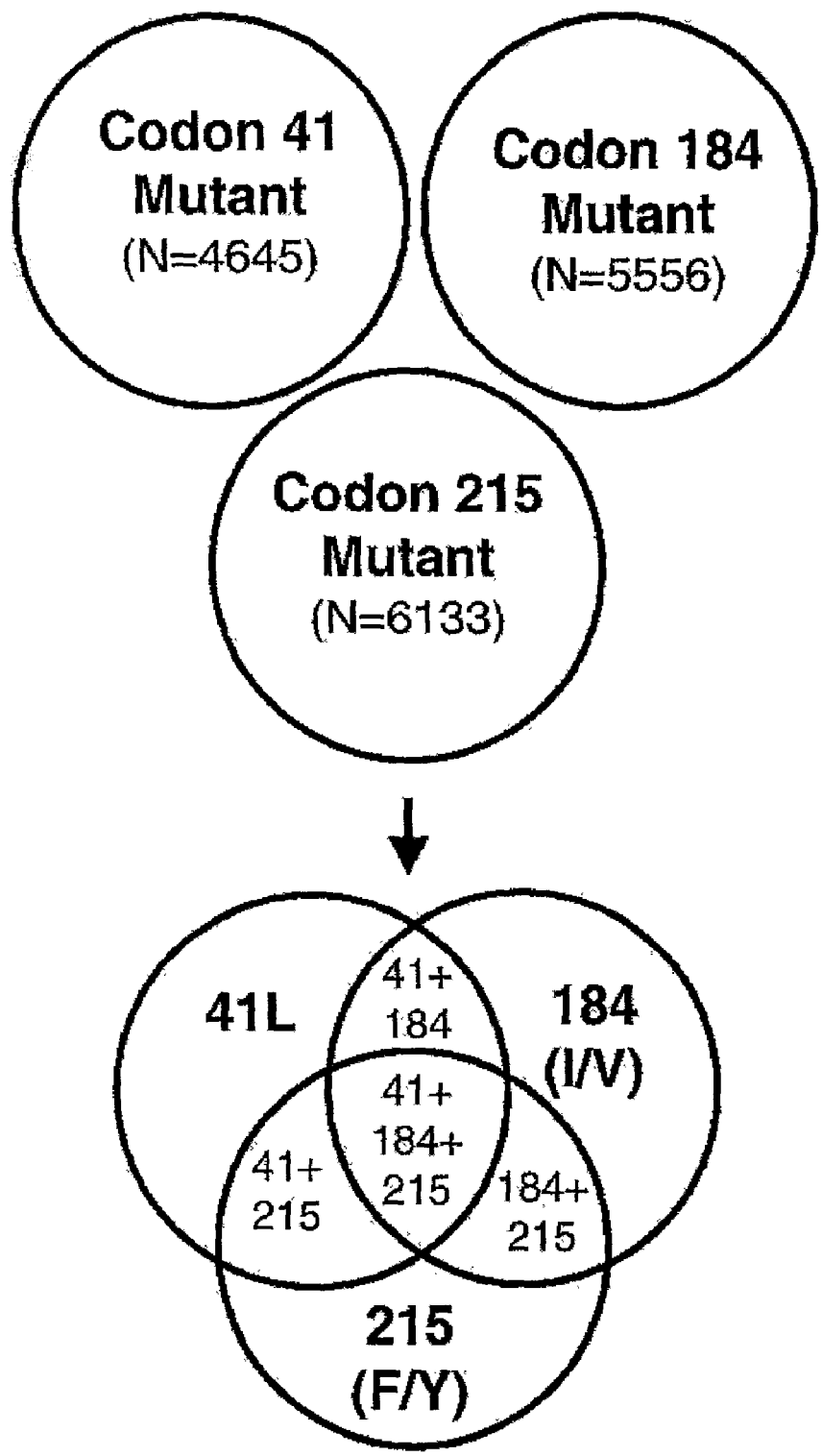
FIG. 7 is a schematic diagram of an exemplary pattern search The numbers indicated for each mutation (N) indicate the N observed in the database analysis illustrated in Table 1.

As with the actual phenotype on which it is based, this was expressed as a fold change in the 50% inhibitory concentration ($IC_{50}$) compared with a value of 1.0 for fully sensitive, wild type virus. FIG. 7 shows diagrammatically how such a search was performed, using mutations that influence resistance to zidovudine (AZT) as an example. This illustration is for a virus that has any combination of the 41L, 184V or I and 215Y or F mutations. A series of searches first find all samples that individually contain each of the mutations and then by an inclusion process, all samples containing the three illustrated mutations are identified.

Corresponding information from the database for these specific AZT resistance mutations is shown in Table 2. This illustrates examples of the first 13255 genotypically-matched samples found in the database for single and multiple mutations at HIV-1 RT codons 41, 184 and 215. A number of interesting characteristics are indicated in this Table. In particular, the phenotypic effect of a mutation depends upon the genetic context in which it occurs. In this simple example of only these three mutations, viruses with 41L can have an average increase in resistance ranging from 1.3-fold to >27-fold. Thus, simple detection of the presence (or absence) of a given mutation can be uninformative or even misleading. Further, the effect of mutations is not simply additive—the modulating effects of the M184V or I mutations (decreasing AZT susceptibility) and/or the 41L mutation (increasing AZT susceptibility) on viruses with the 215Y or F mutations can be discerned from Table 2 (range 6.2 to 27.7-fold). This analysis is considerably less sophisticated than the virtual phenotype system as it represents groups of samples where only the inclusion of three specific mutations has occurred, rather than the additional inclusion and exclusion of other mutations.

TABLE 2

Example of Method for Deriving AZT Virtual Phenotypes (using only three mutations).

| Codon 41 | Codon 184 | Codon 215 | Geometric Mean Phenotype | Average Phenotype (log) | Standard Deviation (log) | N |
| --- | --- | --- | --- | --- | --- | --- |
| ANY | ANY | ANY | 3.9 | 0.59 | 0.78 | 13255 |
| WT | WT | WT | 1.3 | 0.12 | 0.38 | 4826 |
| WT | WT | F/Y | 13.4 | 1.13 | 0.73 | 695 |
| WT | V/I | WT | 1.3 | 0.10 | 0.47 | 2172 |
| WT | V/I | F/Y | 6.2 | 0.79 | 0.61 | 673 |

TABLE 2-continued

Example of Method for Deriving AZT Virtual Phenotypes (using only three mutations).

| Codon 41 | Codon 184 | Codon 215 | Geometric Mean Phenotype | Average Phenotype (log) | Standard Deviation (log) | N |
|---|---|---|---|---|---|---|
| L | WT | WT | 1.7 | 0.24 | 0.36 | 54 |
| L | WT | F/Y | 27.7 | 1.44 | 0.69 | 1783 |
| L | V/I | WT | 1.3 | 0.13 | 0.45 | 75 |
| L | V/I | F/Y | 15.2 | 1.18 | 0.69 | 2693 |

In the actual derivation of a Virtual Phenotype for AZT, a total of 18 mutations was examined in this fashion.

Identification of Genetic Clusters with Distinct Phenotypes

Figure 8:
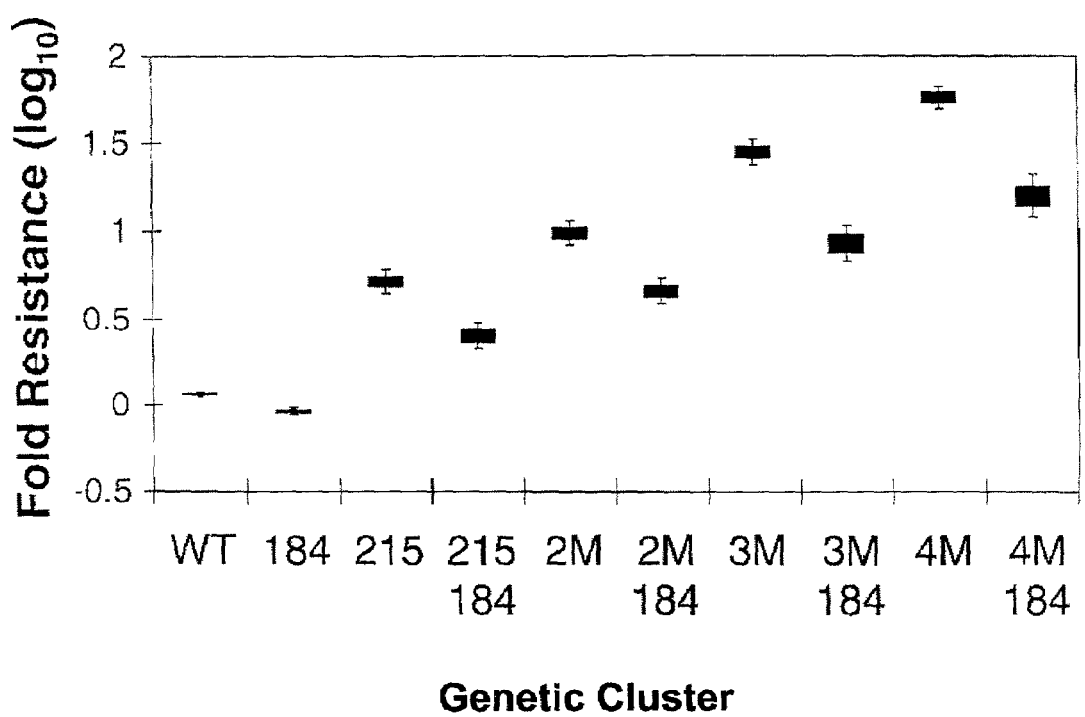
FIG. 8 depicts the phenotypic search results for virus with different clusters of AZT resistance mutations. The graph shows the mean (○), standard error (■) and 95% confidence limits (⊥) for each cluster.

If the search process were functioning appropriately, a large series of phenotypically distinct genetic clusters should be identified. Each of these should have distinguishable phenotypes with only modest variability in susceptibility. This was evaluated by examining the genetic clusters formed by the combinations of AZT mutations described in Table 2. In addition to these mutations, clusters were identified that also contained additional AZT-resistance mutations. These clusters and the corresponding AZT resistance phenotypes are shown in FIG. 8. Searches of the relational genotype/phenotype database were performed using samples with specific AZT resistance mutations, with or without the 3TC resistance mutations, 184V or I. The numbers of samples in each genetic cluster were as follows: WT (wild type, susceptible), 3798; 184 (184V/I), 777; 215 (215Y/F), 175; 215 184 (215Y/F and 184V/I), 70; 2M (41L and 215Y/F), 243; 2M 184 (41L, 215Y/F and 184V/I), 186; 3M (41L, 210W and 215Y/F), 289; 3M 184 (41L, 210W, 215Y/F and 184V/I); 4M (41L, 67N, 210W and 215Y/F), 358; 4M 184 (41L, 67N, 210W, 215Y/F and 184V/I), 84.

This illustrates a number of important points regarding the database searches. Firstly, different genetic clusters have distinct susceptibility profiles (indicated by mean fold resistance values, together with the standard error and 95% confidence intervals). These values range from a slightly reduced level of susceptibility (virus harbouring the 184V mutation) to almost 100-fold increases, due to multiple mutations conferring AZT resistance. Secondly, in each case, the inclusion of the 184V mutation together with AZT resistance mutations, caused a substantial reduction in the predicted magnitude of AZT resistance. The data clearly shows that the pattern recognition system can predict altered susceptibility due to interactions of mutations.

Correlation Between Predicted and Actual Phenotype

Figure 9:
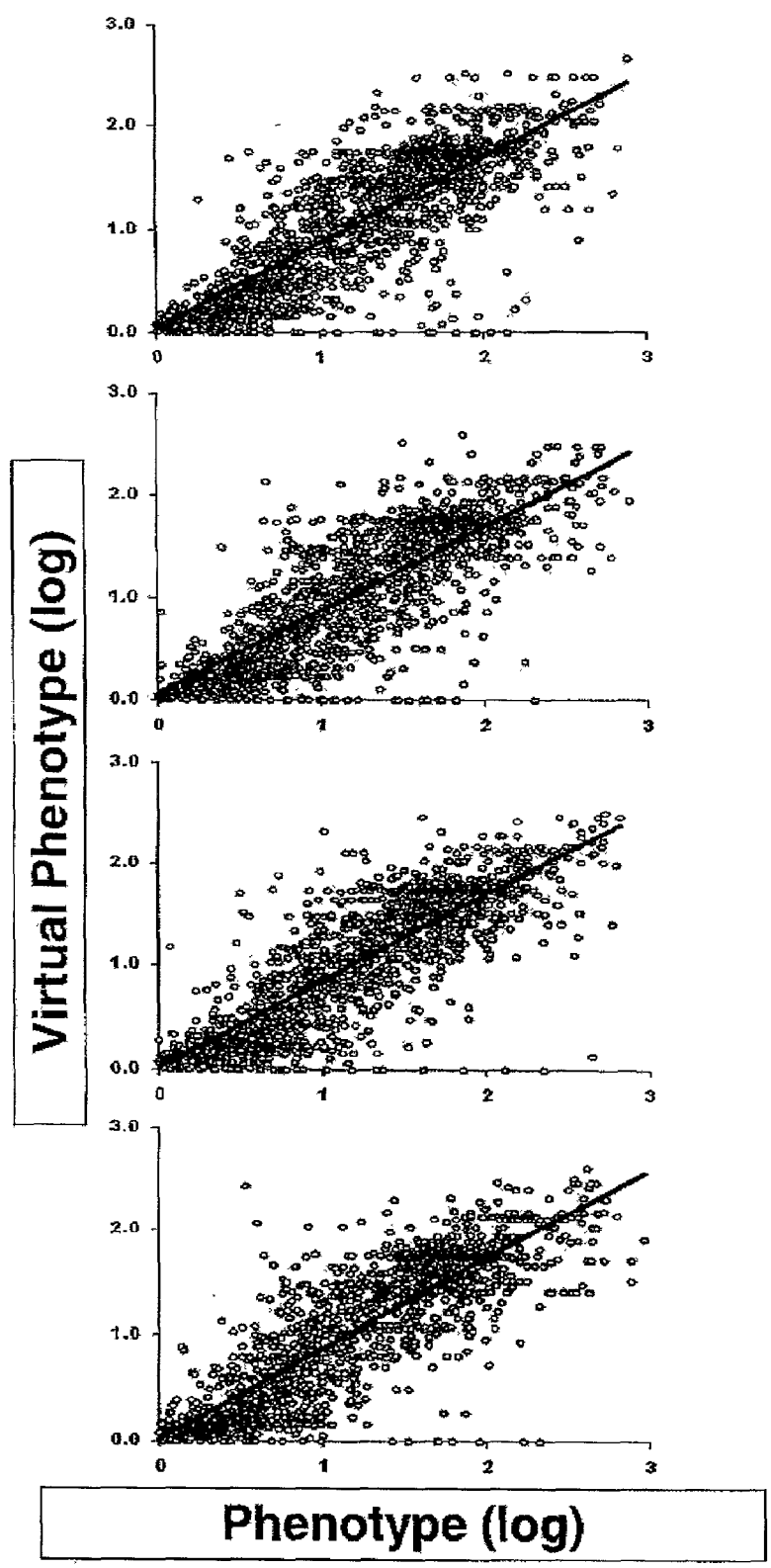
FIG. 9 is a correlation between the actual and computer predicted virtual phenotype. A linear regression analysis is shown for four independent random data sets comprising 500 samples each.

The virtual phenotype was validated in a number of ways. Firstly, between 2700 and 8700 genotypically wild type samples were tested for each drug. As anticipated, the predicted fold change was close to one for all drugs examined, with a range of 0.66–1.69 fold. Next, the quantitative relationship between the predicted phenotypes and actual phenotypes was investigated. 5000 clinically-derived samples from the USA were randomly selected from the resistance database from 1999 onwards and the phenotypic predictions obtained from the genotypic profiles for each drug were compared to actual phenotypes in 10 random subsets of 500 samples each. This resulted in approximately 70,000 determinations in total. Independent linear regression analyses were then performed on each of these data sets (four of these analyses are shown in FIG. 9). These showed a good correlation between the virtual phenotype (mean fold change in $IC_{50}$ value) and actual drug susceptibility phenotype, with an average slope of 0.83 (range 0.81–0.85), intercept of 0.05 (range 0.02–0.07) and average correlation coefficient of 0.87 (range 0.86–0.89) across the ten groups of 500 clinical samples.

The Virtual Phenotype Predicts Clinical Response

The predictive value of the virtual phenotype was also tested. To address this, a retrospective analysis of clinical and virological data from the clinical study, VIRA 3001. Cohen, C., et al., *XIII International AIDS Conference. Durban.* (2000) was performed. This is a recently completed prospective, randomized, clinical trial that demonstrated the positive effect of phenotypic drug resistance information on virological response in patients who had failed a PI-containing therapeutic regimen.

Samples from 191 patients in this study were re-analysed to test the relationship between the virtual phenotype (from genetic sequence) and virological outcome at 16 weeks. The predictive values of phenotype, virtual phenotype and genotype with 'rules-based' interpretation, were analysed according to a data analysis plan (DAP) used by the international resistance collaborative group to re-analyse clinical trials. DeGruttola V., et al., *Antiviral Therapy* 5, 41–48 (2000). This analysis system comprises univariate and multivariate statistical approaches and requires the use of a 'rules-based' mutation list for genotypic interpretation. The results of this analysis are shown in FIG. 10. Logistic regression was used to model the parameter of virological failure at week 16 (defined as plasma HIV-1 RNA above 400 copies/ml). Univariate (a) or multivariate (b) models were used for the drug susceptibility phenotype (phenotype), virtual phenotype (virtual) or genotype. The calculated phenotypic sensitivity score (PSS) or genotypic sensitivity score (GSS) were derived separately for a drop outs as censored (DAC) or drop outs as failures (DAF) analysis. Results of the regression analysis are shown on the FIG. 10 as an odds ratio (OR) of failure to achieve a viral load reduction below 400 copies/ml, with the 95% confidence interval (CI).

Figure 10A:
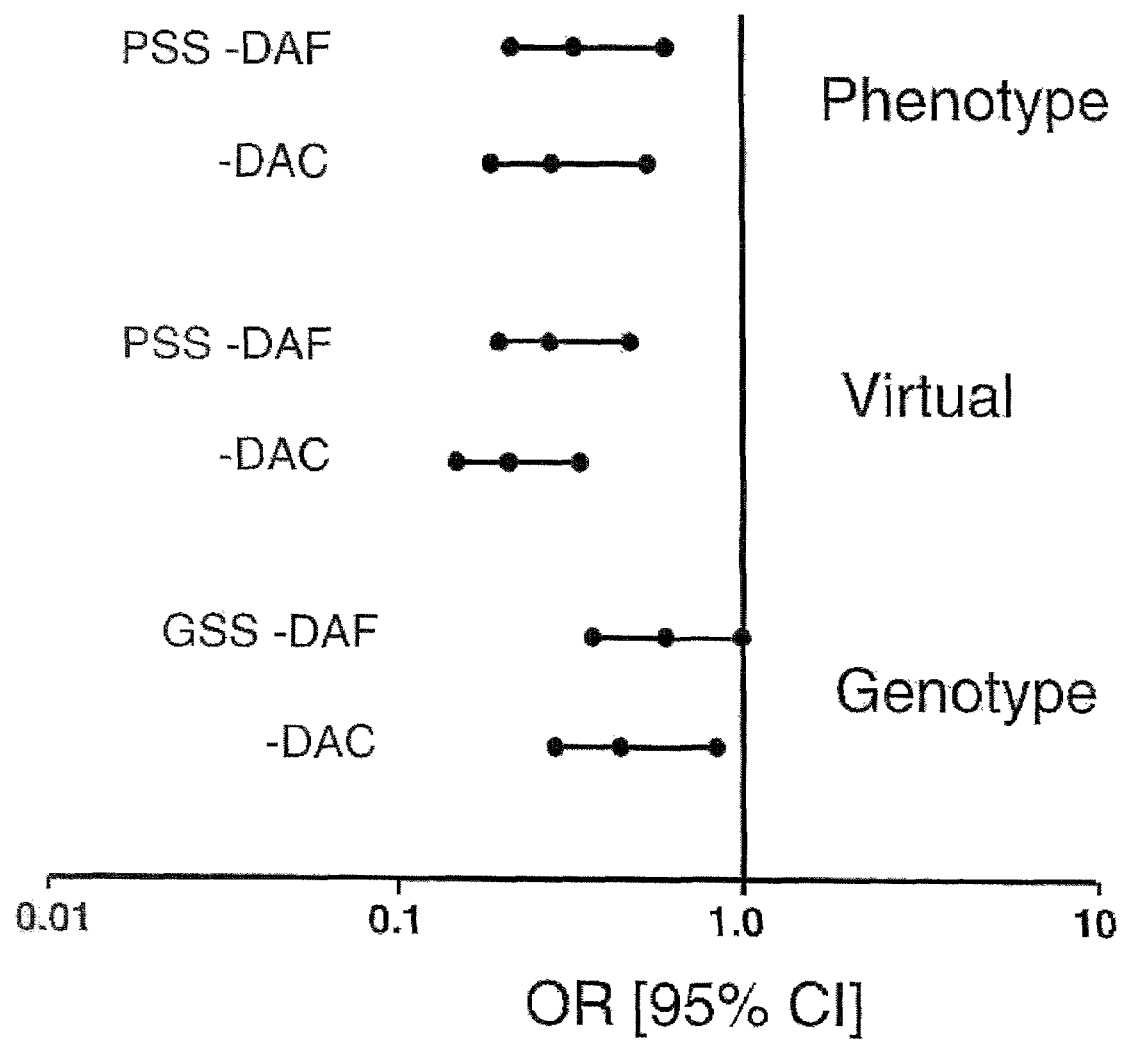
FIGS. 10(a) & (b) are a depiction of the odds ratios of failure to achieve a viral load reduction below 400 viral RNA copies/ml.
Figure 10B:
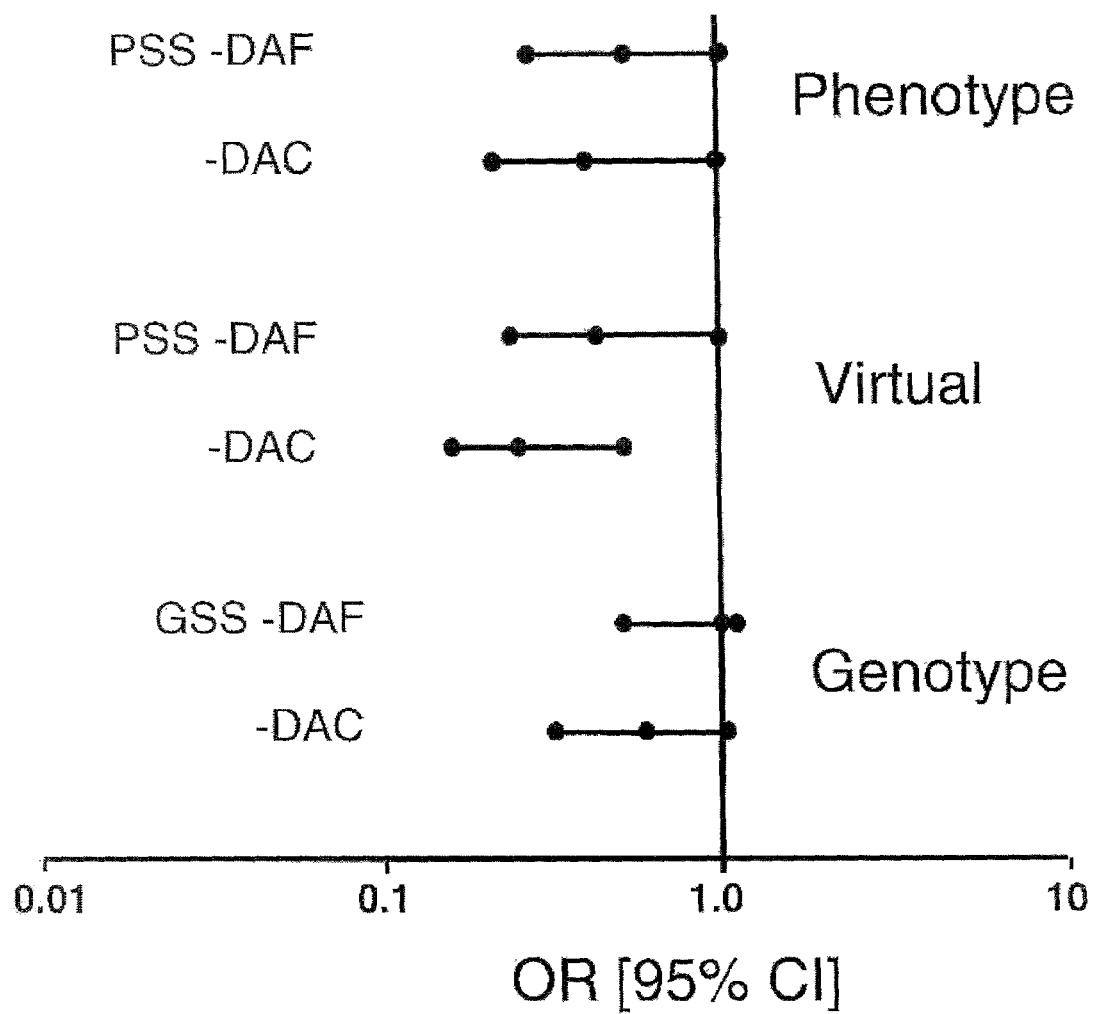

In the univariate model, the genotype analysis (dropouts as censored, DAC) was a significant predictor of response with an odds ratio (OR) of 0.69 (CI=0.51–0.93), p=0.015 (FIG. 10a). However, the genotype was not a significant predictor of response in the multivariate model, OR=0.81 (CI=0.57–1.14), p=0.22 (FIG. 10b). In contrast, the virtual phenotype was highly significant in both models, also using the DAC analysis. With a 4-fold susceptibility cut-off for all drugs in the univariate model, the OR=0.38 (CI=0.25–0.6), p<0.0001 and in the multivariate model the OR=0.52 (CI=0.31–0.87), p=0.013. Using recently defined, drug-specific, biological cut offs, the predictive power of the virtual phenotype was even more significant. Larder, B. A. & Harrigan, P. R., *Fifth International Congress on Drug Therapy in HIV Infection, Glasgow* (2000).

The OR in the univariate model was 0.39 (CI=0.26–0.58), p<0.0001, and in the multivariate model the OR=0.49 (CI=0.31–0.76), p=0.0014. The DAF (dropouts as failures) analyses showed consistent superiority for the predicted phenotype over genotype although the level of significance was correspondingly lower for all of the categories (FIG. 10).

All references, patents, and patent applications cited herein are incorporated by reference in their entirety.

We claim:

1. A method of determining a phenotype of a retrovirus, wherein the retrovirus is the Human Immunodeficiency Virus, comprising:
   a) obtaining from a patient a sample comprising at least one of a plasma sample, a blood sample, a saliva sample, mucous sample, and a tissue sample;
   b) obtaining a genetic sequence of the Human Immunodeficiency Virus from the patient sample;
   c) identifying a mutation pattern of the genetic sequence of the Human Immunodeficiency Virus, wherein said mutation pattern comprises at least one mutation that correlates to resistance to at least one therapy;
   d) searching a relational genotype/phenotype database for at least one database mutation pattern similar to said mutation pattern of the genetic sequence of the Human Immunodeficiency Virus;
   e) obtaining at least one database phenotype of the at least one database mutation pattern; and
   f) determining the phenotype of the Human Immumunodeficiency Virus from the at least one database phenotype.

2. The method of claim 1, wherein a series of phenotypes is obtained by repeating steps b) through e) for each therapy in a group of therapies.

3. The method of claim 1, wherein said mutation pattern of the genetic sequence of the Human Immunodeficiency Virus is specific to a therapy.

4. The method of claim 1, wherein said at least one mutation is chosen from a frame shift mutation, a base substitution, and an epigenetic mutation.

5. The method of claim 1, wherein the genetic sequence of Human Immunodeficiency Virus is the genetic sequence of the protease region of the Human Immunodeficiency Virus genome, the genetic sequence of the reverse transcriptase region of the Human Immunodeficiency Virus genome, or the genetic sequence of the protease region and reverse transcriptase region of the Human Immunodeficiency Virus genome.

6. The method of claim 1, wherein said mutation pattern of the genetic sequence of the Human Immunodeficiency Virus comprises at least two mutations that correlate to resistance to at least one therapy.

7. The method of claim 1, wherein the search of the relational genotype/phenotype database for at least one sample with a similar mutation pattern uses cluster searches.

8. The method of claim 1, wherein the database mutation pattern comprises at least one mutation found in said mutation pattern of the genetic sequence of the Human Immunodeficiency Virus.

9. The method of claim 1, wherein the database mutation pattern is a mutation pattern in which at least about 50% of the mutations are identical to said mutation pattern of the genetic sequence of the Human Immunodeficiency Virus.

10. The method of claim 9, wherein the database mutation pattern is a mutation pattern in which at least about 80% of the mutations are identical to said mutation pattern of the genetic sequence of the Human Immunodeficiency Virus.

11. The method of claim 10, wherein the database mutation pattern is a mutation pattern in which at least about 90% of the mutations are identical to said mutation pattern of the genetic sequence of the Human Immunodeficiency Virus.

12. The method of claim 11, wherein the mutations of the database mutation pattern are identical to said mutation pattern of the genetic sequence of the Human Immunodeficiency Virus.

13. The method of claim 1, wherein the phenotype of the Human Immunodeficiency Virus is a mean fold-change in resistance, wherein said mean fold change is obtained from all of the database phenotypes obtained in step d).

14. The method of claim 1, wherein the phenotype of the Human Immunodeficiency Virus is expressed as an $IC_{50}$.

15. A method of reporting a phenotype for a Human Immunodeficiency Virus, comprising generating a report having the phenotype determined using the method of claim 1.

16. A method of determining a phenotype of a retrovirus, wherein the retrovirus is the Human Immunodeficiency Virus comprising:
   a) obtaining from a patient a sample comprising at least one of a plasma sample, a blood sample, a saliva sample, mucous sample, and a tissue sample;
   b) obtaining a genetic sequence of the Human Immunodeficiency Virus from the patient sample;
   c) searching a relational genotype/phenotype database for at least one database genetic sequence similar to said genetic sequence of the Human Immunodeficiency Virus;
   d) obtaining a database phenotype of the at least one database genetic sequence; and
   e) determining the phenotype of the Human Immunodeficiency Virus from the database phenotype.

17. The method of claim 16, wherein the at least one database genetic sequence is at least about 60% identical to the genetic sequence of the Human Immunodeficiency Virus.

18. The method of claim 17, wherein the at least one database genetic sequence is at least about 70% identical to the genetic sequence of the Human Immunodeficiency Virus.

19. The method of claim 18, wherein the at least one database genetic sequence is at least about 80% identical to the genetic sequence of the Human Immunodeficiency Virus.

20. The method of claim 19, wherein the at least one database genetic sequence is at least about 90% identical to the genetic sequence of the Human Immunodeficiency Virus.

21. A computer program for determining a phenotype of a retrovirus, wherein the retrovirus is the Human Immunodeficiency Virus, wherein the program is comprised on a computer readable medium, comprising:
   a) receiving a genetic sequence from the Human Immunodeficiency Virus from a patient;
   b) identifying a mutation pattern of the genetic sequence of the Human Immunodeficiency Virus, wherein said mutation pattern comprises at least one mutation that correlates to resistance to at least one therapy;
   c) searching a relational genotype/phenotype database for at least one database mutation pattern similar to said mutation pattern of the genetic sequence of the Human Immunodeficiency Virus;
   d) obtaining at least one database phenotype of the at least one database mutation pattern from the relational genotype/phenotype database;
   e) determining the at least one phenotype of Human Immunodeficiency Virus from the at least one database phenotype; and
   f) displaying the phenotype of the Human Immunodeficiency Virus sample.

22. The computer program of claim 21, wherein a series of phenotypes is obtained by repeating steps b) through e) for a group of therapies.

23. The computer program of claim 22, wherein the phenotype of the Human Immunodeficiency Virus is provided in a report.

* * * * *

UNITED STATES PATENT AND TRADEMARK OFFICE
CERTIFICATE OF CORRECTION

PATENT NO. : 7,206,699 B2
APPLICATION NO. : 09/836477
DATED : April 17, 2007
INVENTOR(S) : Brendan Larder et al.

It is certified that error appears in the above-identified patent and that said Letters Patent is hereby corrected as shown below:

Column 4,
Line 41, delete "judgement" and insert -- judgment --.

Column 11,
Line 3, delete "may" and insert -- may be --.

Signed and Sealed this

Eighth Day of July, 2008

JON W. DUDAS
*Director of the United States Patent and Trademark Office*